(12) United States Patent
Alshaer et al.

(10) Patent No.: US 9,949,667 B2
(45) Date of Patent: Apr. 24, 2018

(54) MASK AND METHOD FOR USE IN RESPIRATORY MONITORING AND DIAGNOSTICS

(71) Applicant: UNIVERSITY HEALTH NETWORK, Toronto (CA)

(72) Inventors: Hisham Alshaer, Mississauga (CA); Geoffrey Roy Fernie, Etobicoke (CA); T. Douglas Bradley, Toronto (CA); Oleksandr Igorovich Levchenko, Mississauga (CA); Steven M. Pong, Etobiocoke (CA)

(73) Assignee: University Health Network, Toronto (CA)

( * ) Notice: Subject to any disclaimer, the term of this patent is extended or adjusted under 35 U.S.C. 154(b) by 344 days.

(21) Appl. No.: 13/710,160

(22) Filed: Dec. 10, 2012

(65) Prior Publication Data

US 2013/0172772 A1     Jul. 4, 2013

Related U.S. Application Data

(63) Continuation-in-part of application No. 12/888,237, filed on Sep. 22, 2010, and a continuation-in-part of
(Continued)

(51) Int. Cl.
*A61B 5/087*     (2006.01)
*A61B 7/00*     (2006.01)
(Continued)

(52) U.S. Cl.
CPC .............. *A61B 5/087* (2013.01); *A61B 5/097* (2013.01); *A61B 5/4818* (2013.01); *A61B 7/003* (2013.01); *A61B 5/7257* (2013.01)

(58) Field of Classification Search
CPC .... A61M 16/06; A61M 16/0683; A61B 7/003
See application file for complete search history.

(56) References Cited

U.S. PATENT DOCUMENTS

| | | | |
|---|---|---|---|
| 4,648,407 A | 3/1987 | Sackner | |
| 5,671,733 A | 9/1997 | Raviv et al. | |

(Continued)

FOREIGN PATENT DOCUMENTS

| | | |
|---|---|---|
| CA | 2501607 | 4/2004 |
| CA | 2190488 | 4/2007 |

(Continued)

OTHER PUBLICATIONS

Alshaer et al., "Development and validationof an algorithm for detection of apneas and hyponeas using overnight breath sound recordings," *American J. of Resp. Crit. Care Med.*, vol. 183, Meeting Abstracts A6317, D108 Diagnosis and Management of Sleep Disorders, Poster Discussion Session URL: http://aireem.atsjournals.org/cgi/reprint/183/1_meetingabstracts/A6317, (2011).

(Continued)

*Primary Examiner* — Etsub Berhanu
*Assistant Examiner* — Michael Catina
(74) *Attorney, Agent, or Firm* — Middleton Reutlinger

(57) ABSTRACT

Disclosed is a mask for use in respiratory monitoring and/or diagnostics. The mask comprises at least one transducer responsive to sound and/or airflow for generating a signal, and a support structure to rest on the subject's face. In one embodiment, the support structure comprises two or more limbs that provide a transducer support for supporting the transducer at a distance from a nose and mouth area, allowing monitoring via the transducer of sound and/or airflow produced by the subject. Also described is a mask comprising a transducer responsive to airflow for generating a signal and a support structure to rest on the subject's face
(Continued)

and extend outwardly over a nose and mouth area to provide a transducer support supporting the transducer at a distance from a nose and mouth area of the subject's face and at a preset orientation, for monitoring via the transducer of airflow produced by the subject.

20 Claims, 28 Drawing Sheets

Related U.S. Application Data application No. PCT/CA2011/000555, filed on May 17, 2011, said application No. 12/888,237 is a continuation-in-part of application No. PCT/CA2009/001644, filed on Nov. 16, 2009.

(60) Provisional application No. 61/272,460, filed on Sep. 25, 2009, provisional application No. 61/193,320, filed on Nov. 17, 2008.

(51) Int. Cl.
*A61B 5/097* (2006.01)
*A61B 5/00* (2006.01)

(56) References Cited

U.S. PATENT DOCUMENTS

| | | | |
|---|---|---|---|
| 5,782,240 | A | 7/1998 | Raviv et al. |
| 5,797,852 | A | 8/1998 | Karakasoglu et al. |
| 5,845,636 | A * | 12/1998 | Gruenke et al. ......... 128/204.23 |
| 5,961,447 | A | 10/1999 | Raviv et al. |
| 6,045,514 | A | 4/2000 | Raviv et al. |
| 6,142,950 | A * | 11/2000 | Allen et al. .................... 600/529 |
| 6,171,258 | B1 | 1/2001 | Karakasoglu et al. |
| 6,213,955 | B1 | 4/2001 | Karakasoglu et al. |
| 6,290,654 | B1 | 9/2001 | Karakasoglu |
| 6,368,287 | B1 | 4/2002 | Hadas |
| 6,375,623 | B1 | 4/2002 | Gavriely |
| 6,491,642 | B1 | 12/2002 | Stasz |
| 6,705,315 | B2 * | 3/2004 | Sullivan ................. A61B 5/097 128/204.18 |
| 7,118,536 | B2 | 10/2006 | Haberland et al. |
| 7,225,021 | B1 | 5/2007 | Park et al. |
| 7,387,124 | B2 | 6/2008 | Noda et al. |
| 7,785,265 | B2 | 8/2010 | Schätzl |
| 7,850,619 | B2 | 12/2010 | Gavish et al. |
| 2002/0123699 | A1 | 9/2002 | Lambert et al. |
| 2005/0222502 | A1 | 10/2005 | Cooper |
| 2006/0196510 | A1 * | 9/2006 | McDonald et al. ..... 128/206.21 |
| 2008/0243017 | A1 | 10/2008 | Moussavi et al. |
| 2008/0308105 | A1 | 12/2008 | Alder et al. |
| 2008/0319333 | A1 | 12/2008 | Gavish et al. |
| 2009/0118631 | A1 | 5/2009 | Gavish et al. |
| 2009/0293880 | A1 | 12/2009 | Rutan |
| 2011/0092839 | A1 | 4/2011 | Alshaer et al. |

FOREIGN PATENT DOCUMENTS

| | | |
|---|---|---|
| WO | WO 01/15602 | 3/2001 |
| WO | 0143804 | 6/2001 |
| WO | WO 01/93743 | 12/2001 |
| WO | WO2004041084 A1 | 5/2004 |
| WO | WO 06/008745 | 1/2006 |
| WO | WO 2006/008745 | 1/2006 |
| WO | WO 2008122806 A1 * | 10/2008 ........... A61B 5/0816 |
| WO | WO 2010/054481 | 5/2010 |
| WO | WO2010054481 A1 | 5/2010 |
| WO | WO 2011/010384 | 1/2011 |
| WO | 2011082346 | 11/2011 |
| WO | WO 2012/058727 | 5/2012 |
| WO | 2012155251 | 11/2012 |
| WO | 2012155257 | 11/2012 |

OTHER PUBLICATIONS

Nakano et al., "Automatic detection of sleep-disordered breathing fro a single-channel airflow record," *European Respiratory Journal*, 29(4): 728-736 (2007).

Varady et al., "A novel method for the detection of apnea and hypopnea events in respiration signals," *IEEE Transactions on Biomedical Engineering*, 49(9): 936-942 (2002).

Werthammer et al., "Apnea monitoring by acoustic detection of airflow," *Pediatrics*, 71(1): 53-55 (1983).

International Search Report issued in application No. PCT/CA2012/000494 (dated 2012).

International Search Report issued in application No. PCT/CA2012/000478 (dated 2012).

Yao et al.: 'The Design of a Real-Time Accelerometer-Based Sleeping Position Monitoring System and its Application on Obstructive Sleep Apnea Syndrome.' 2012 International Conference on Systems and Informatics (ICSAI 2012) May 19, 2012, pp. 1061-1066 May 19, 2012.

Hofsoy et al.: 'Monitoring and therapy of sleep-related breathing disorders.' 6th International Workshop on Wearable Micro and Nano Technologies for Personalized Health (pHealth) Jun. 24-26, 2009, pp. 41-44.

Van Kesteren et al."Quantitative Effects of Trunk and Head Position on the Apnea Hypopnea Index in Obstructive Sleep Apnea." Sleep, vol. 34, No. 8, Aug. 1, 2011, pp. 1075-1081.

International Search Report for PCT Application No. PCT/US2014/000009; dated May 1, 2014.

Abeyratne et al., "Pitch jump probability measures for the analysis of snoring sounds in apnea," *Physiological Measurement*, vol. 26, pp. 779-798, 2005.

Alshaer et al., "Adaptive segmentation and normalization of breathing acoustic data of subjects with obstructive sleep apnea," Paper presented at: *Science and Technology for Humanity (TIC-STH)*, 2009, IEEE Toronto International Conference; Sep. 26-27, 2009.

Alshaer et al., "Phase Tracking of the Breathing Cycle in Sleeping Subjects by Frequency Analysis of Acoustic Data," *International Journal of Healthcare Technology and Management*, vol. 11:3, pp. 163-175 (2010).

Argod, et al., "Differentiating Obstructive and Central Sleep Respiratory Events through Pulse Transit Time," *Am. J. Respir. Crit. Care Med.*, vol. 158:6, pp. 1778-1783 (1998).

Arzt et al., "Association of sleep-disordered breathing and the occurrence of stroke," *Am J Respir Crit Care Med*, vol. 172, pp. 1447-1451 (2005).

Bieger-Farhan et al., "Portable method for the determination of snoring site by sound analysis," Journal of Laryngology & Otology, vol. 118, pp. 135-138 (2004).

Bradley et al., "Sleep apnea and heart failure: Part I: obstructive sleep apnea," Circulation, vol. 107, pp. 1671-1678, Apr. 1, 2003.

Campbell et al., "The perception of wakefulness within sleep," *Sleep*, vol. 4, pp. 177-183 (1981).

Cavusoglu et al., "Investigation of sequential properties of snoring episodes for obstructive sleep apnoea identification," *Physiol Meas.*, vol. 29:8, pp. 879-898 (2008).

Dalmay et al., "Acoustic Properties of the Normal Chest," *Eur. Resp. Jrnl.*, vol. 8, pp. 1761-1769 (1995).

Duckitt et al., "Automatic detection, segmentation and assessment of snoring from ambient acoustic data," *Physiological Measurement*, vol. 27, pp. 1047-1056 (2006).

Fiz et al., "Analysis of forced wheezes in asthma patients," *Respiration*, vol. 73, pp. 55-60, (2006).

Fiz et al., "Detection of wheezing during maximal forced exhalation in patients with obstructed airways," *Chest*, vol. 122, pp. 186-191 (2002).

Fiz et al., "Acoustic analysis of snoring sound in patients with simple snoring and obstructive sleep apnea," *European Respiratory Journal*, vol. 9, pp. 2365-2370 (1996).

Fiz et al., Wheezing identification in asthma subjects during forced exhalation, *American Journal of Respiratory and Critical Care Medicine*, vol. 159, p. A652 (1999).

(56) References Cited

OTHER PUBLICATIONS

Folke et al., "Critical review of non-invasive respiratory monitoring in medical care," *Med Biol Eng Comput*, vol. 41, pp. 377-383 (2003).
Fritsch et al., "Monotone piecewise cubic interpolation," *SIAM Journal on Numerical Analysis*, vol. 17, pp. 238-246 (1980).
Gavriely et al., "Parametric representation of normal breath sounds," *J Appl Physiol*, vol. 73:5, pp. 1776-1784 (1992).
Guler et al., "Two-stage classification of respiratory sound patterns," *Comput Biol Med*, vol. 35, pp. 67-83 (2005).
Harrington et al., *Techniques in Speech Acoustics: Kluwer Academic Publisher* (1999).
Hill et al., "Palatal snoring identified by acoustic crest factor analysis," *Physiological Measurement*, vol. 20, pp. 167-174 (1999).
Hoffstein et al., "Snoring: is it in the ear of the beholder?" *Sleep*, vol. 17, pp. 522-526 (1994).
Hult et al., "A bioacoustic method for timing of the different phases of the breathing cycle and monitoring of breathing frequency," *Med Eng Phys*, vol. 22, pp. 425-433 (2000).
Hult et al., "An improved bioacoustic method for monitoring of respiration," *Technol Health Care*, vol. 12, pp. 323-332 (2004).
Jane et al., "Analysis of wheezes in asthmatic patients during spontaneous respiration," *Conf Proc IEEE Eng Med Biol Soc*, vol. 5, p. 3836 (2004).
Jane et al., "Automatic detection of snoring signals: Validation with simple snorers and OSAS patients," *Proceed of the 22nd Annual EMBS Int'l Conf.*, pp. 3129-3130 (2000).
Jane et al., "Automatic snoring signal analysis in sleep studies," *Proceed of the 25th Annual Int'l Conf of the IEEE EMBS*, Cancun, Mexico, pp. 366-369 (2003).
Leung et al., "Sleep apnea and cardiovascular disease," *Am J Respir Crit Care Med*, vol. 164, pp. 2147-2165 (2001).
MacKay, "Information Theory, Inference & Learning Algorithms," Cambridge, UK: *Cambridge University Press*, ch. 20, pp. 284-286 (2003).
Mattei et al., "Diagnosis of sleep apnea," *Minerva Med*, vol. 95, pp. 213-231 (2004).
Michael et al., "Analysed snoring sounds correlate to obstructive sleep disordered breathing," *European Archives of Oto-Rhino-Laryngology*, vol. 265:1, pp. 105-113 (2008).
Ng et al., "Could formant frequencies of snore signals be an alternative means for the diagnosis of obstructive sleep apnea?" *Sleep Medicine*, vol. 9:8, pp. 894-898 (2008).
Ng et al., "Role of upper airway dimensions in snore production: Acoustical and perceptual findings," *Annals of Biomedical Engineering.*, vol. 37:9, pp. 1807-1817 (2009).
Nieto et al., "Association of sleep-disordered breathing, sleep apnea, and hypertension in a large community-based study. Sleep Heart Health Study," *Jama*, vol. 283, pp. 1829-1836 (2000).
Perez-Padilla et al., "Characteristics of the snoring noise in patients with and without occlusive sleep apnea," *American Review of Respiratory Disease*, vol. 147:3, pp. 635-644 (1993).
Quinn et al., "The differentiation of snoring mechanisms using sound analysis," *Clinical Otolaryngology & Allied Sciences*, vol. 21, pp. 119-123 (1996).
Rabiner et al., "Fundamentals of Speech Recognition," *Prentice Hall*, p. 100-103 (1993).
Radfar et al., "A maximum likelihood estimation of vocal-tract-related filter characteristics for single channel speech separation," *EURASIP Journal on Audio, Speech, and Music Processing*, vol. 2007, Art. ID 84186, pp. 1-15 (2007).
Rechtschaffen et al., "A Manual of Standardized Terminology, Techniques and Scoring System for Sleep Stages of Human Subjects," *Los Angeles: UCLA Brain Information Service/Brain Research Institute* (1968).
Sankur et al., "Comparison of AR-based algorithms for respiratory sounds classification," *Comput Biol Med*, vol. 24, pp. 67-76 (1994).
Sankur et al., "Multiresolution biological transient extraction applied to respiratory crackles," *Comput Biol Med*, vol. 26, pp. 25-39 (1996).
Sen et al., "A multi-channel device for respiratory sound data acquisition and transient detection," *Conf Proc IEEE Eng Med Biol Soc*, vol. 6, pp. 6658-6661 (2005).
Shahar et al., "Sleep-disordered breathing and cardiovascular disease: cross-sectional results of the Sleep Heart Health Study," *Am J Respir Crit Care Med*, vol. 163, pp. 19-25 (2001).
Shiota et al., "Alterations in upper airway cross-sectional area in response to lower body positive pressure in healthy subjects," *Thorax*, vol. 62, No. 10, pp. 868-872, Oct. 2007.
"Sleep-related breathing disorders in adults: recommendations for syndrome definition and measurement techniques in clinical research," The Report of an American Academy of Sleep Medicine Task Force, *Sleep*. 1999;22(5):667-689.
Sola-Soler et al., "Pitch analysis in snoring signals from simple snorers and patients with obstructive sleep apnea in Engineering in Medicine and Biology," *24th Annual Conf and the Annual Fall Mtg of the Biomedi Engineer Soc, EMBS/BMES Conf. Proceedings of the Second Joint* (2002).
Sola-Soler et al., "Variability of snore parameters in time and frequency domains in snoring subjects with and without Obstructive Sleep Apnea," *Conf Proc IEEE Eng Med Biol Soc*, vol. 3, pp. 2583-2586 (2005).
Steltner et al., "Diagnosis of Sleep Apnea by Automatic Analysis of Nasal Pressure and Forced Oscillation Impedance," *Am. J. Respir. Crit. Care Med.*, vol. 165:7, pp. 940-944 (2002).
Stock et al., "Development and application of a real-time monitoring and feedback system for deep inspiration breath hold based on external marker tracking," *Medical physics.*, vol. 33:8, p. 2868 (2006).
Thomas et al., "Differentiating Obstructive from Central and Complex Sleep Apnea Using an Automated Electocardiogram-Based Method," *Sleep*, vol. 30:12, pp. 1756-1769 (2007).
Vegfors et al., "Presentation and evaluation of a new optical sensor for respiratory rate monitoring," *Int J Clin Monit Comput*, vol. 11, pp. 151-156 (1994).
Wakwella et al., "Automatic Segmentation and Pitch/Jitter Tracking of Sleep Disturbed Breathing Sounds," *8th International Conf on Control, Automation, Robotics and Vision*, Kunming, China., *IEEE*, p. 936-940 (2004).
Xiong et al., "Problems in Timing of Respiration with the Nasal Thermistor Technique," *J Am Soc of Echocardio*, vol. 6:2, pp. 210-216 (1993).
Yeginer et al., "Modeling of pulmonary crackles using wavelet networks," *Conf Proc IEEE Eng Med Biol Soc*, vol. 7, pp. 7560-7563 (2005).
Young et al., "The occurrence of sleep-disordered breathing among middle-aged adults," *N Engl J Med*, vol. 328, pp. 1230-1235 (1993).
Young et al., "Estimation of the clinically diagnosed proportion of sleep apnea syndrome in middle-aged men and women," *Sleep*, vol. 20, pp. 705-706 (1997).
Yu et al., "A simple respiration gating technique and its application in high-resolution PET camera," *IEEE Transactions on Nuclear Science*, vol. 52:1, p. 125 (2005).
Int'l Search Report & Written Opinion issued in application No. PCT/CA09/01644 (dated 2010).
International Preliminary Report on Patentability issued in Int'l Patent Application No. PCT/CA2009/001644 (dated 2010).
International Search Report issued in Int'l Patent Application No. PCT/CA2011/000555 (dated 2011).
Extended European Search Report, European Patent Application No. 11826237.7, dated Mar. 29, 2017.

* cited by examiner

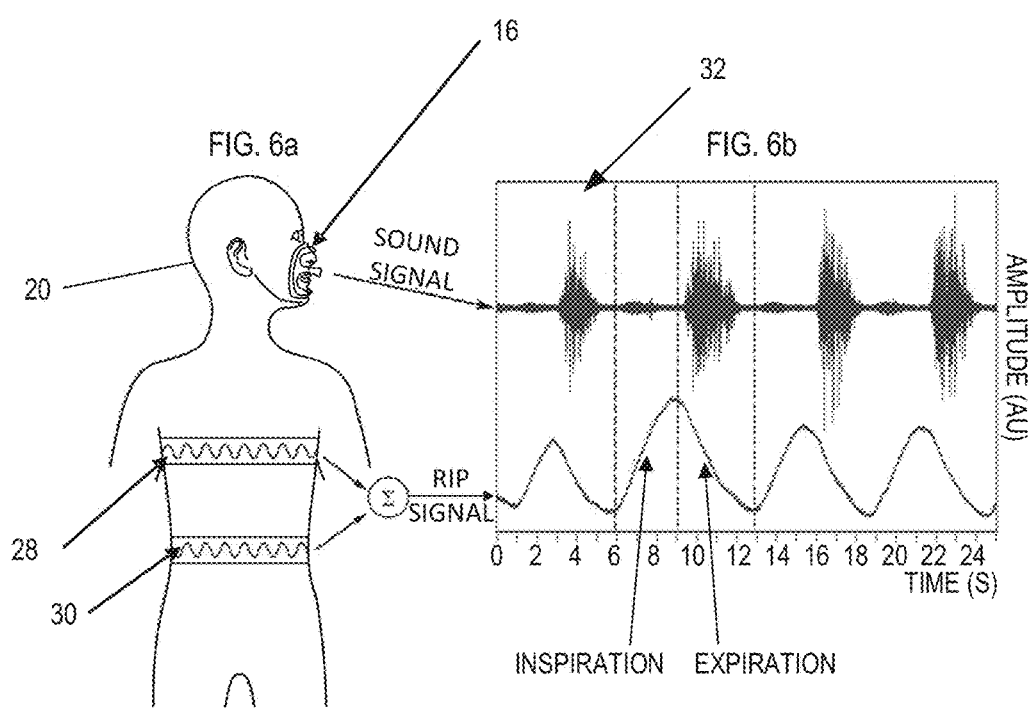

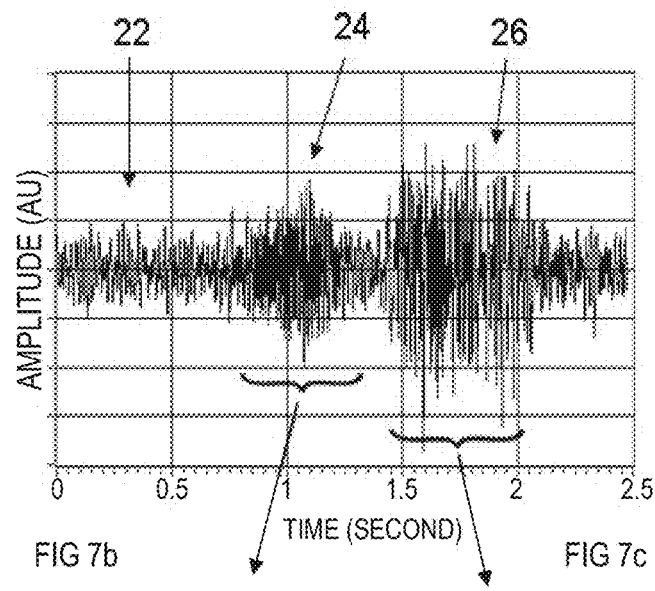
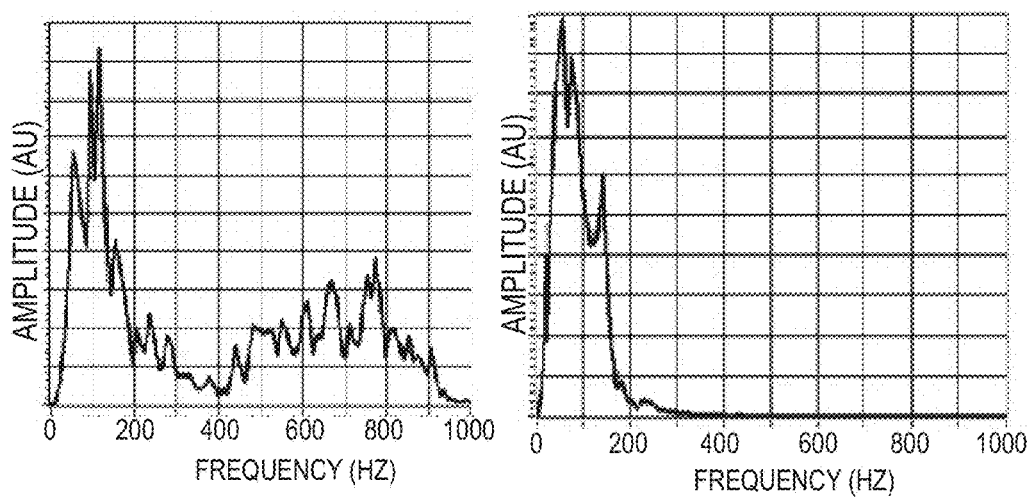
FIG 7a
FIG 7b
FIG 7c

MASK AND METHOD FOR USE IN RESPIRATORY MONITORING AND DIAGNOSTICS

CROSS REFERENCE TO RELATED APPLICATIONS

This application is a Continuation-in-Part of copending international patent application no. PCT/CA2011/000555, filed May 17, 2011, and is a Continuation-in-Part of U.S. patent application Ser. No. 12/888,237, filed Sep. 22, 2010, which is a Continuation-in-Part of international application no. PCT/CA2009/001644, filed Nov. 16, 2009, which claims the benefit of priority under 35 U.S.C. § 119(e) to U.S. Provisional Patent Application No. 61/193,320, filed Nov. 17, 2008. U.S. patent application Ser. No. 12/888,237 also claims the benefit of priority under 35 U.S.C. § 119(e) to U.S. Provisional Patent Application No. 61/272,640, filed Sep. 25, 2009. The disclosures set forth in the referenced applications are incorporated herein by reference in their entireties, including all information as originally submitted to the United States Patent and Trademark Office.

FIELD OF THE DISCLOSURE

The present disclosure relates to respiratory diagnostic and monitoring systems, and in particular, to a mask and method for use in respiratory monitoring and diagnostics.

BACKGROUND

Several clinical conditions require close monitoring of respiratory activity including respiratory failure, respiratory tract infections as well as respiratory depression associated with anesthesia and sedatives. Also, respiratory disorders are known to disturb sleep patterns. For example, recurrent apneas and hypopnea lead to intermittent hypoxia that provokes arousals and fragmentation of sleep, which in turn may lead to restless sleep, and excessive daytime sleepiness. Repetitive apneas and intermittent hypoxia may also elicit sympathetic nervous system activation, oxidative stress and elaboration of inflammatory mediators which may cause repetitive surges in blood pressure at night and increase the risk of developing daytime hypertension, atherosclerosis, heart failure, and stroke independently from other risks.

There remains a need for improved tools and methods for monitoring respiratory activity, for example in a clinical setting, or again in diagnosing and/or monitoring respiratory disorders, as discussed above, in order to reduce or even obviate the risks that may be associated therewith.

Namely, while some have proposed diagnostic tools and methods for diagnosing, monitoring and/or generally investigating certain breathing disorders, these tools and methods are often particularly invasive and/or uncomfortable for the subject at hand, and therefore, can yield unsatisfactory results. For instance, many diagnostic procedures are solely implemented within a clinical environment, which amongst other deficiencies, do not allow for monitoring a subject in its natural environment, leading to skewed or inaccurate results, or in the least, forcing the subject through an unpleasant and mostly uncomfortable experience.

Alternatively, different portable devices have been suggested for the diagnosis of sleep apneas; however, these solutions generally require the subject to position and attach several wired electrodes themselves in the absence of a health care provider. Unfortunately, subject-driven electrode positioning and installation often leads to a reduction in subject comfort and compliance, and increases the chance that the electrodes will be detached or displaced in use. Since accurate positioning and installation of such electrodes are paramount to proper diagnostics, captured signals in such situations are often unreliable, a measure which can only effectively be determined once the data is transferred back to a health center, at which point, such data, if properly identified, must be withdrawn from the study. Furthermore, such devices regularly need to be shipped back to the health center for processing and, given their generally invasive nature, for hygienic reconditioning, e.g. disinfection.

Similarly, in a clinical setting, while the positioning and attachment of monitoring electrodes may be completed by an experienced health care professional, the devices currently used in such settings generally at best leave the subject physically wired to one or more monitoring devices, if not via more invasive techniques, which wiring can be a particular nuisance to the subjects general comfort and mobility, and obtrusive to individuals or health care practitioners maneuvering around the subject. For example, International Application Publication No. WO 01/15602 describes a clinical system wherein a microphone is suspended from the ceiling above the subject, the recorded data of which is combined with readings from an esophageal pressure catheter and nasal airflow monitoring.

Less intrusive methods have been proposed, for example in U.S. Pat. No. 5,797,852, wherein a microphone is suspended from a base device sitting on the headboard of the subject's bed to record sound produced by the subject's breathing, which base device further comprises a second microphone to record ambient noise in the subject's room. Clearly, the accuracy of the recordings is highly dependent on the subject's position, which will most likely vary during a given sleeping period. Other examples found in U.S. Pat. No. 6,142,950 and US Patent Application Publication No. 2002/0123699 provide facially mounted devices configured for either airflow or sound recordal, respectively. While these latter devices may be less dependent on subject positioning, they are equally limited in the type of data acquired for processing, as only one of airflow or sound can be accessed by any one of these designs. Similarly, International Application Publication No. WO 2006/008745 describes the use of a standard headset having a microphone disposed in front of the subject's mouth to monitor expiratory airflow, with other subject driven and ambient sounds being expressly filtered out as parasitical to the intended system. Furthermore, each of the above examples proposes a configurationally limited design that generally suffers from various deficiencies which, in operation, limit its effectiveness in capturing accurate and usable data.

Accordingly, there is a need for a new mask and method for use in respiratory monitoring and/or diagnostics that overcome some of the drawbacks of known techniques, or at least, that provide the public with a useful alternative. Furthermore, improvements and/or alternative approaches in the type and quality of information collected in monitoring and/or diagnosing a subject, as well as in the methods and procedures implemented in processing and analyzing this information are needed to yield better results without, for example, necessarily requiring further data diversity which, ultimately, can result in greater constraints to the subject's mobility and/or comfort.

This background information is provided to reveal information believed by the applicant to be of possible relevance to the present invention. No admission is necessarily intended, nor should be construed, that any of the preceding information constitutes prior art against the present invention.

SUMMARY

An object of the invention is to provide a mask and method for use in diagnosing breathing disorders. In accordance with an aspect of the invention, there is provided a mask to be worn by a subject on its face for use in respiratory monitoring, the mask comprising: at least one transducer responsive to sound and airflow for generating a data signal representative thereof; and a support structure shaped and configured to rest on the subject's face and thereby delineate a nose and mouth area thereof, and comprising two or more outwardly projecting limbs that, upon positioning the mask, converge into a transducer supporting portion for supporting said at least one transducer at a distance from said area, thereby allowing for monitoring via said at least one transducer of both sound and airflow produced by the subject while breathing.

In accordance with another embodiment of the invention, there is provided a mask to be worn by a subject on its face for use in respiratory monitoring, the mask comprising: a transducer responsive to airflow for generating a data signal representative thereof; and a support structure shaped and configured to rest on the subject's face and thereby delineate a nose and mouth area thereof, and comprising two or more outwardly projecting limbs that, upon positioning the mask, converge into a transducer supporting portion for supporting said transducer at a distance above said area, each of said two or more outwardly projecting limbs having, along at least a portion thereof, an inward-facing channel defined therein for channeling toward said transducer, air flow produced by the subject while breathing, thereby allowing for monitoring of said airflow.

In accordance with another embodiment of the invention, there is provided a method for remotely diagnosing a breathing disorder of a subject, the method comprising the steps of: providing the subject access to a self-contained diagnostic mask to be worn on the subject's face while breathing, said mask comprising at least one transducer responsive to sound and airflow for generating a signal representative thereof, and a recording device operatively coupled thereto; recording on said recording device sound and airflow signals produced by the subject while breathing; transferring said recorded signals to a remotely located diagnostic center for processing; and diagnosing the breathing disorder solely on the basis of said processed sound and airflow signals.

In accordance with another embodiment of the invention, there is provided a mask to be worn by a subject on its face for use in respiratory monitoring, the mask comprising: a transducer responsive to airflow for generating a signal representative thereof; and a support structure shaped and configured to rest on the subject's face and extend outwardly therefrom over a nose and mouth area thereof to provide a transducer supporting portion for supporting said transducer, upon positioning the mask, at a distance from said area and at a preset orientation in relation thereto, thereby allowing for monitoring via said transducer of airflow produced by both the subject's nose and mouth while breathing.

Other aims, objects, advantages and features of the invention will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein:

FIG. 6a is an exemplary set-up of Respiratory Inductance Plethysmogrphy (RIP) on an individual and the microphone and transducer equipment of FIGS. 2a and 2b;

FIG. 6b is an exemplary plot of 25-second long recording of breathing sounds and simultaneous RIP signals from a representative individual wherein the dashed line indicates the separation of inspiration and expiration cycles;

FIG. 7a is a representative digitized raw data breathing sound amplitude versus time plot of a single breathing cycle with the three phases of respiration;

FIG. 7b is a representative frequency spectrum of the inspiration phase of FIG. 7a;

FIG. 7c is a representative frequency spectrum of the expiration phase of FIG. 7a;

DETAILED DESCRIPTION

Figure 1:
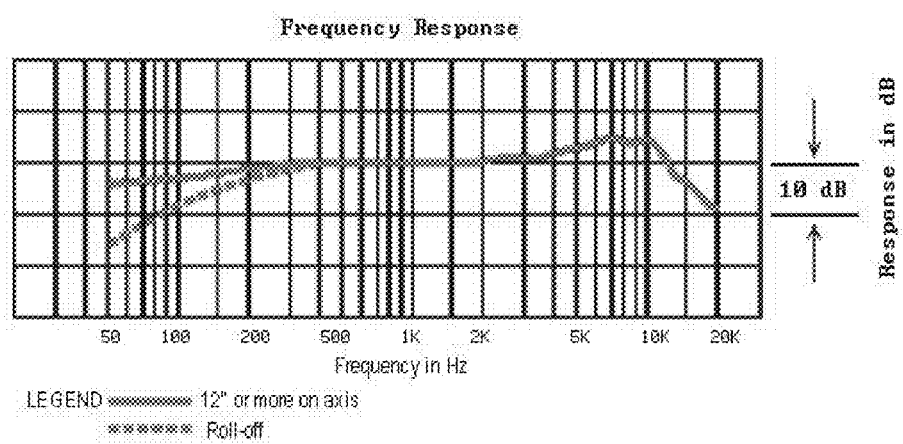
FIG. 1 is a plot of an exemplary microphone response curve of an exemplary embodiment.

It should be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical or electrical connections or couplings. Furthermore, and as described in subsequent paragraphs, the specific mechanical or electrical configurations illustrated in the drawings are intended to exemplify embodiments of the disclosure. However, other alternative mechanical or electrical configurations are possible which are considered to be within the teachings of the instant disclosure. Furthermore, unless otherwise indicated, the term "or" is to be considered inclusive.

With reference to the disclosure herein and the appended figures, a mask and method for use in respiratory monitoring and diagnostics is henceforth described, as well as a method for monitoring, identifying and/or determining characteristics of an individual's breathing, including breathing phases thereof, using a processed acoustic signal data stream collected and/or recorded waveform data. In one example, the waveform data is collected from or is associated with breathing sounds and other sounds from one or more microphones or other sound wave collecting equivalents thereof.

In some embodiments, various systems and methods, or subsystems and procedures, may involve the use of a control unit or other such computing device, in which some or all of its associated components are computer implemented that may be provided in a number of forms. They may be embodied in a software program configured to run on one or more general purpose computers, such as a personal computer, or on a single custom built computer, such as a programmed logic controller (PLC) which is dedicated to the function of the system alone. The system may, alternatively, be executed on a more substantial computer mainframe. The general purpose computer may work within a network involving several general purpose computers, for example those sold under the trade names APPLE or IBM, or clones thereof, which are programmed with operating systems known by the trade names WINDOWS™, LINUX™, MAC O/S™ or other well known or lesser known equivalents of these. The system may involve pre-programmed software using a number of possible languages or a custom designed version of a programming software sold under the trade name ACCESS or other programming software. The computer network may be a wired local area network, or a wide area network such as the Internet, or a combination of the two, with or without added security, authentication protocols, or under "peer-to-peer" or "client-server" or other networking architectures. The network may also be a wireless network or a combination of wired and wireless networks. The wireless network may operate under frequencies such as those dubbed 'radio frequency' or "RF" using protocols such as the 802.11, TCP/IP, BLUE TOOTH and the like, or other well known Internet, wireless, satellite or cell packet protocols. Also, the present method may also be implemented using a microprocessor-based, battery powered device.

Figure 3:
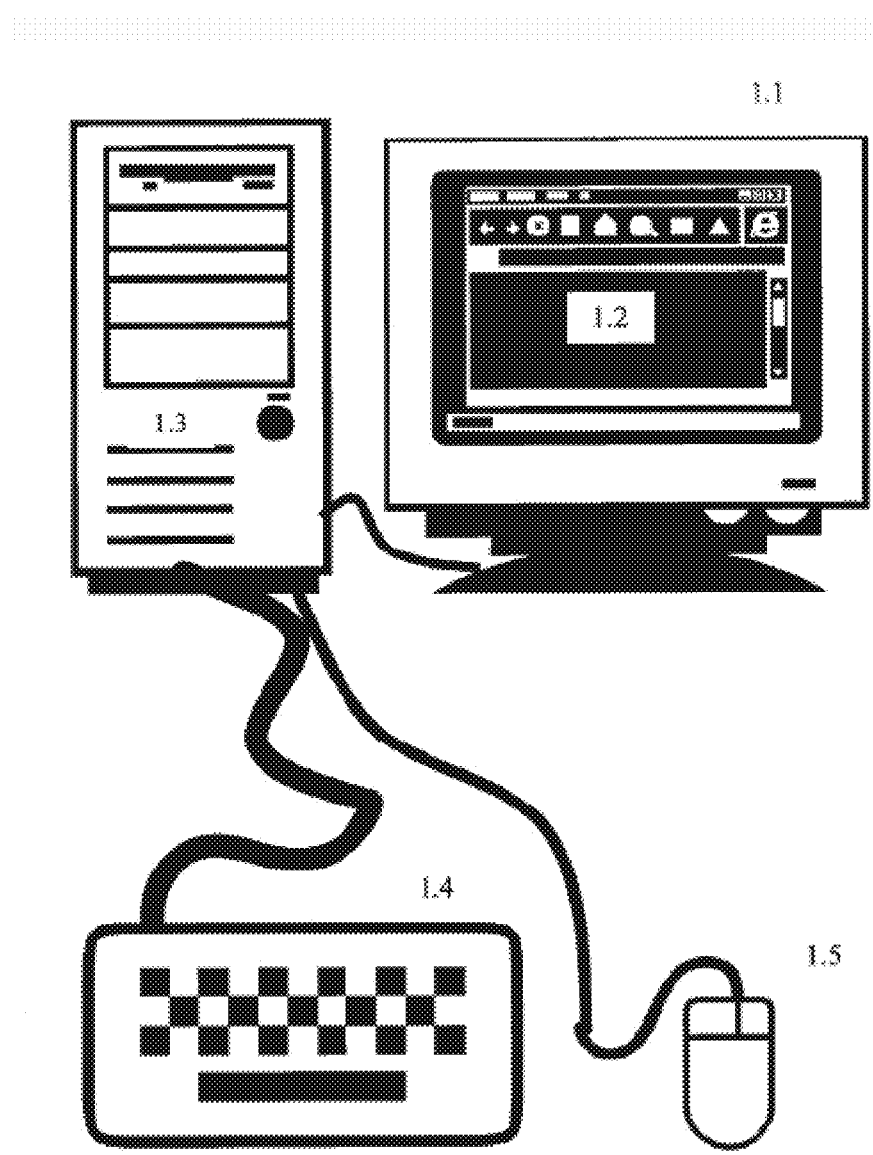
FIG. 3 is a schematic computer system in accordance with an apparatus for transforming breathing sounds in inspiration and expiration phases.

FIG. 3 shows a general computer system on which embodiments may be practiced. The general computer system comprises information relay module (1.1). In some embodiments, the information relay module (1.1) comprises a means for providing audible cues, such as speakers. In some embodiments, the information relay module is comprised of a display device or module (1.1) with a display screen (1.2). Examples of display device are Cathode Ray Tube (CRT) devices, Liquid Crystal Display (LCD) Devices etc. The general computer system can also have other additional output devices like a printer. The cabinet (1.3) houses the additional basic components of the general computer system such as the microprocessor, memory and disk drives. In a general computer system the microprocessor is any commercially available processor of which x86 processors from Intel and 680X0 series from Motorola are examples. Many other microprocessors are available. The general computer system could be a single processor system or may use two or more processors on a single system or over a network. The microprocessor for its functioning uses a volatile memory that is a random access memory such as dynamic random access memory (DRAM) or static memory (SRAM). The disk drives are the permanent storage medium used by the general computer system. This permanent storage could be a magnetic disk, a flash memory and a tape. This storage could be removable like a floppy disk or permanent such as a hard disk. Besides this the cabinet (1.3) can also house other additional components like a Compact Disc Read Only Memory (CD-ROM) drive, sound card, video card etc. The general computer system also includes various input devices such as, for example, a keyboard (1.4) and a mouse (1.5). The keyboard and the mouse are connected to the general computer system through wired or wireless links. The mouse (1.5) could be a two-button mouse, three-button mouse or a scroll mouse. Besides the said input devices there could be other input devices like a light pen, a track ball, etc. The microprocessor executes a program called the operating system for the basic functioning of the general computer system. The examples of operating systems are UNIX™, WINDOWS™ and OS X™. These operating systems allocate the computer system resources to various programs and help the users to interact with the system. It should be understood that the disclosure is not limited to any particular hardware comprising the computer system or the software running on it.

Figure 4:
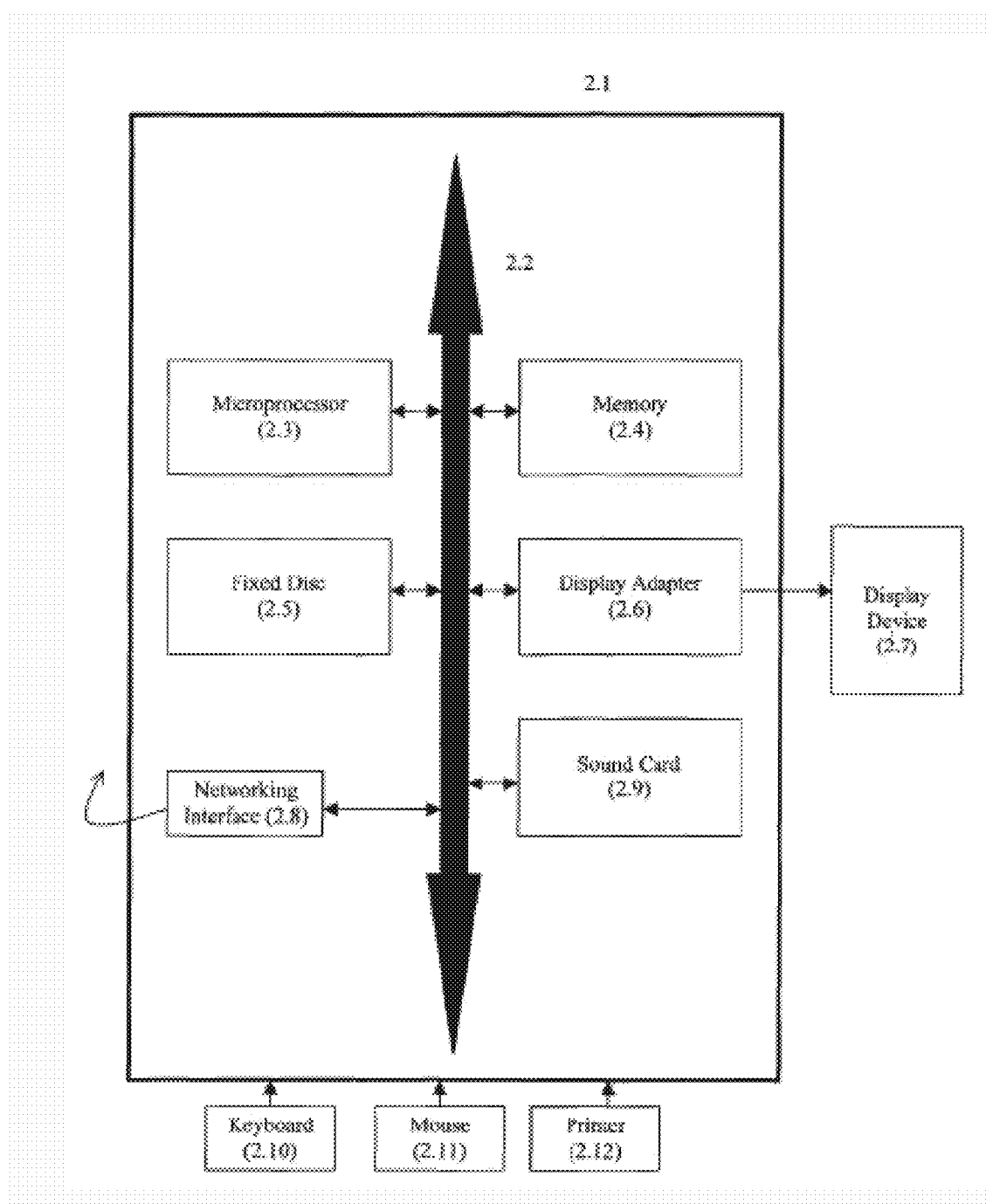
FIG. 4 is a block diagram of a computer system in accordance with the apparatus of FIG. 3.

FIG. 4 shows the internal structure of the general computer system of FIG. 3. The general computer system (2.1) includes various subsystems interconnected with the help of a system bus (2.2). The microprocessor (2.3) communicates and controls the functioning of other subsystems. Memory (2.4) helps the microprocessor in its functioning by storing instructions and data during its execution. Fixed Drive (2.5) is used to hold the data and instructions permanent in nature like the operating system and other programs. Display adapter (2.6) is used as an interface between the system bus and the display device (2.7), which is generally a monitor. The network interface (2.8) is used to connect the computer with other computers on a network through wired or wireless means. The system is connected to various input devices like keyboard (2.10) and mouse (2.11) and output devices like a printer (2.12) or speakers. Various configurations of these subsystems are possible. It should also be noted that a system implementing exemplary embodiments may use less or more number of the subsystems than described above. The computer screen which displays the recommendation results can also be a separate computer system than that which contains components such as database 360 and the other modules described above.

Figure 11:
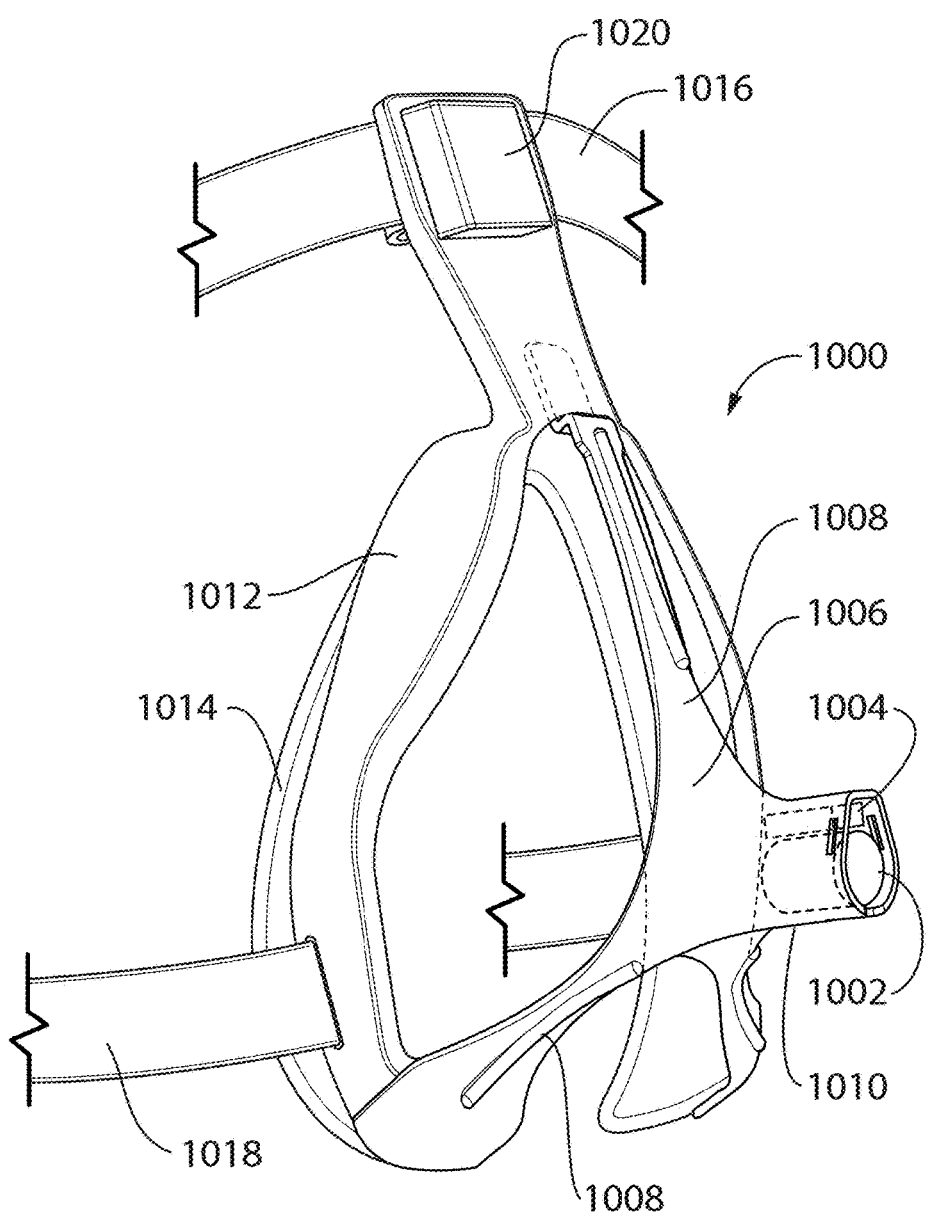
FIG. 11 is a perspective view of a mask for use in respiratory monitoring and/or diagnostics, in accordance with one embodiment of the invention.
Figure 12:
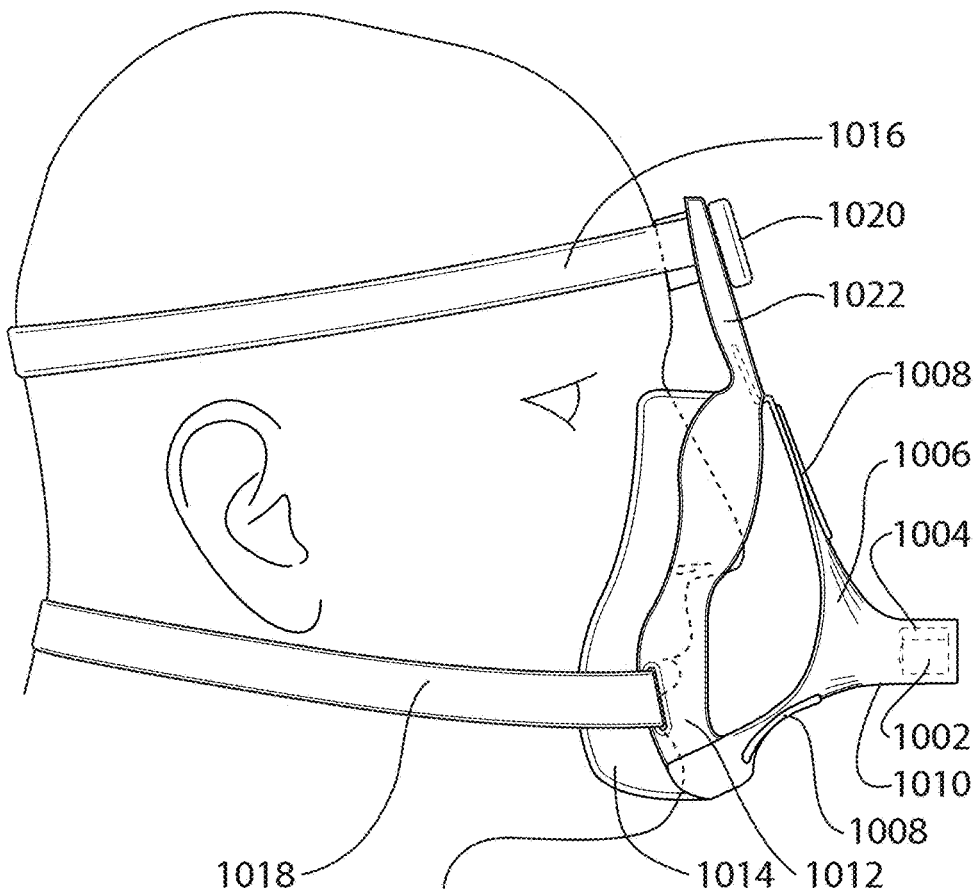
FIG. 12 is a side view of the mask of FIG. 11 when positioned on a subject's face, in accordance with one embodiment of the invention.
Figure 13:
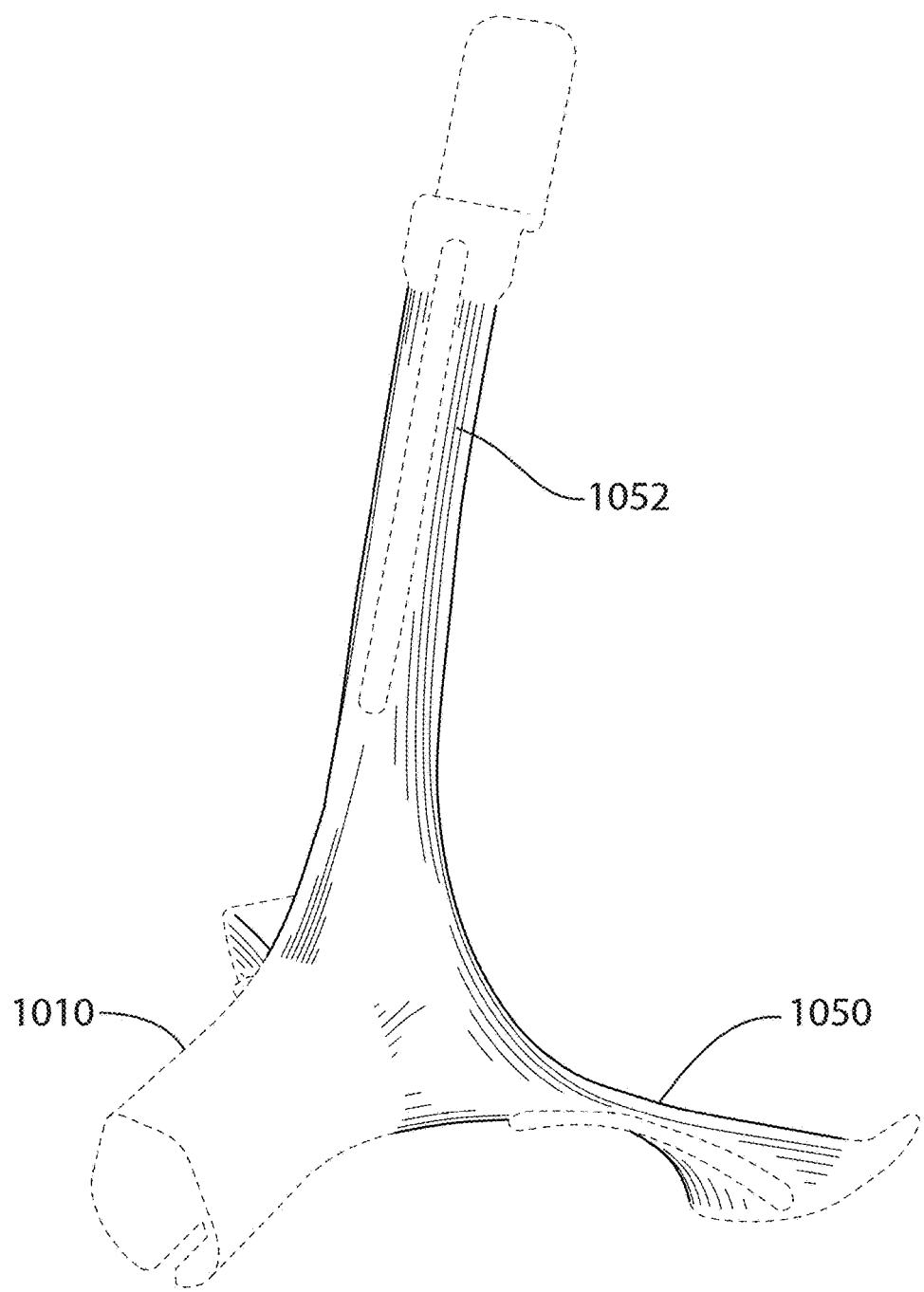
FIG. 13 is a front perspective view of an outwardly projecting portion of a respiratory monitoring and/or diagnostic mask, for example as shown in FIG. 11, showing in stippled lines limb extremities and reinforcements, and a transducer supporting extension thereof.
Figure 14:
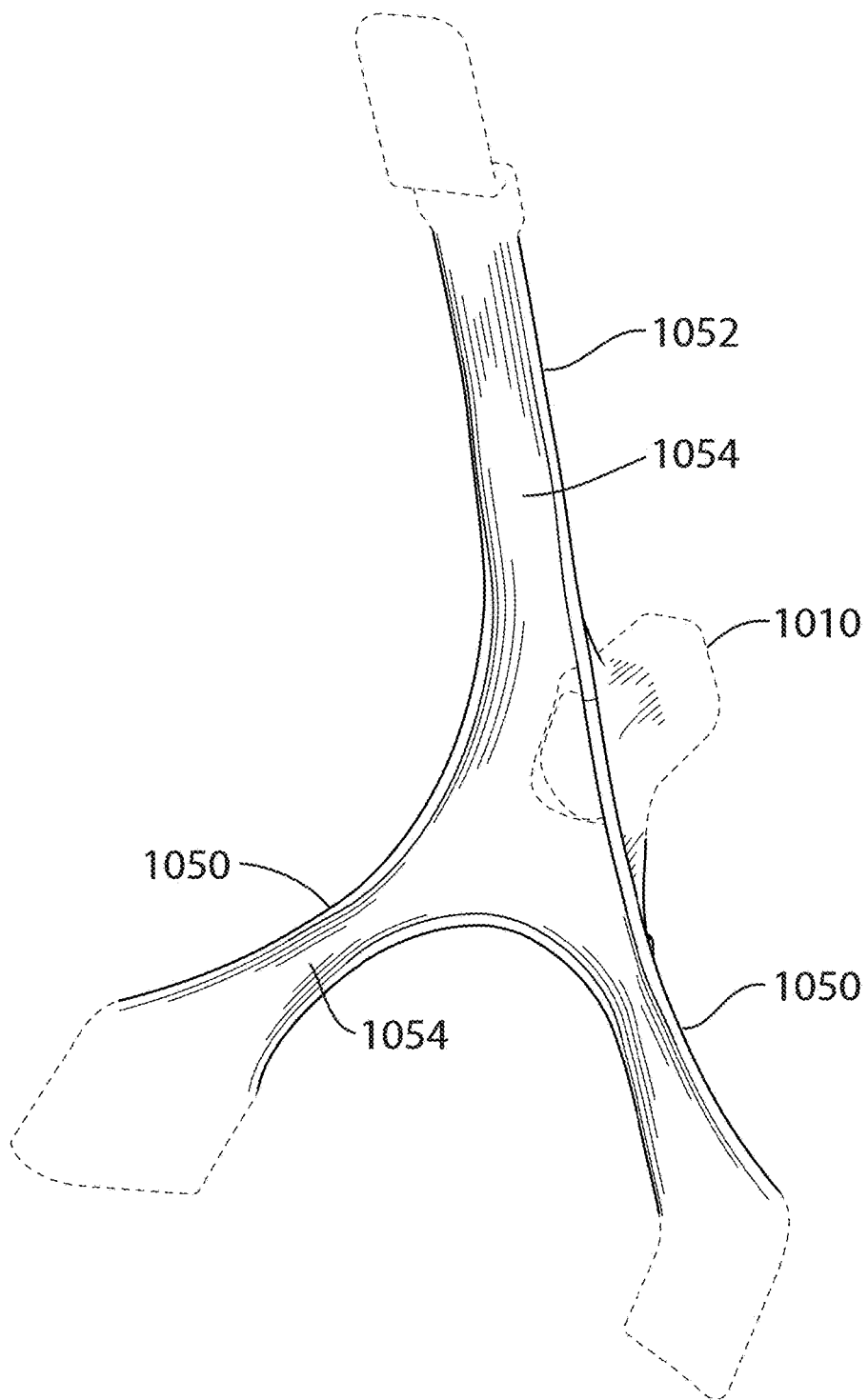
FIG. 14 is a rear perspective view of the outwardly projecting portion of FIG. 13.
Figure 15:
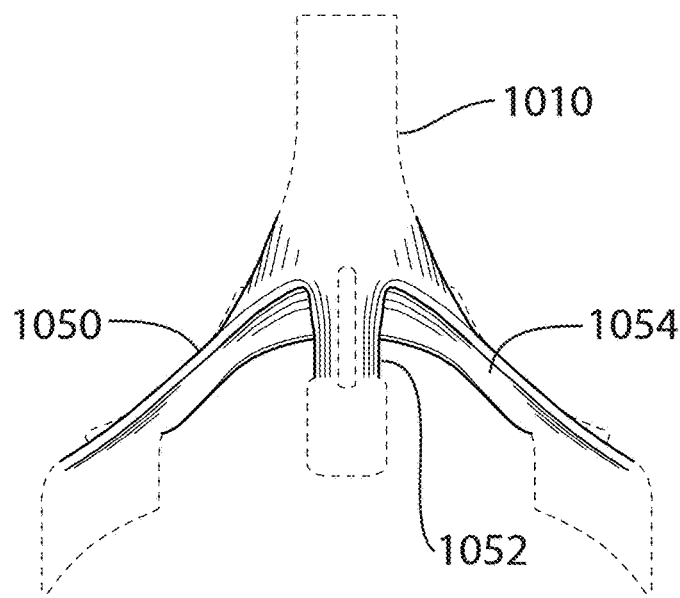
FIG. 15 is a top plan view of the outwardly projecting portion of FIG. 13.
Figure 16:
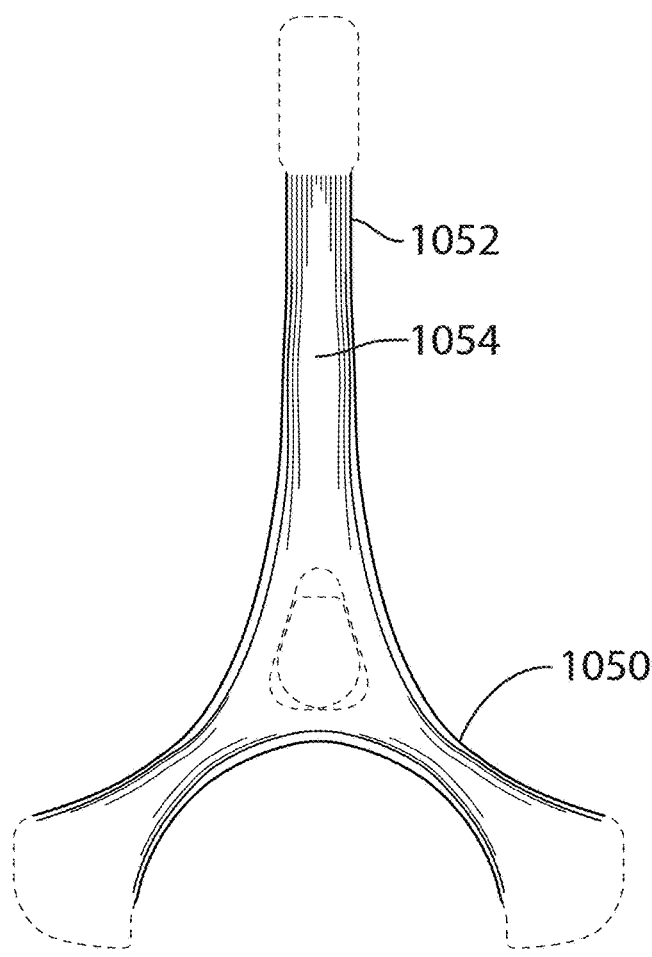
FIG. 16 is a rear view of the outwardly projecting portion of FIG. 13.
Figure 17:
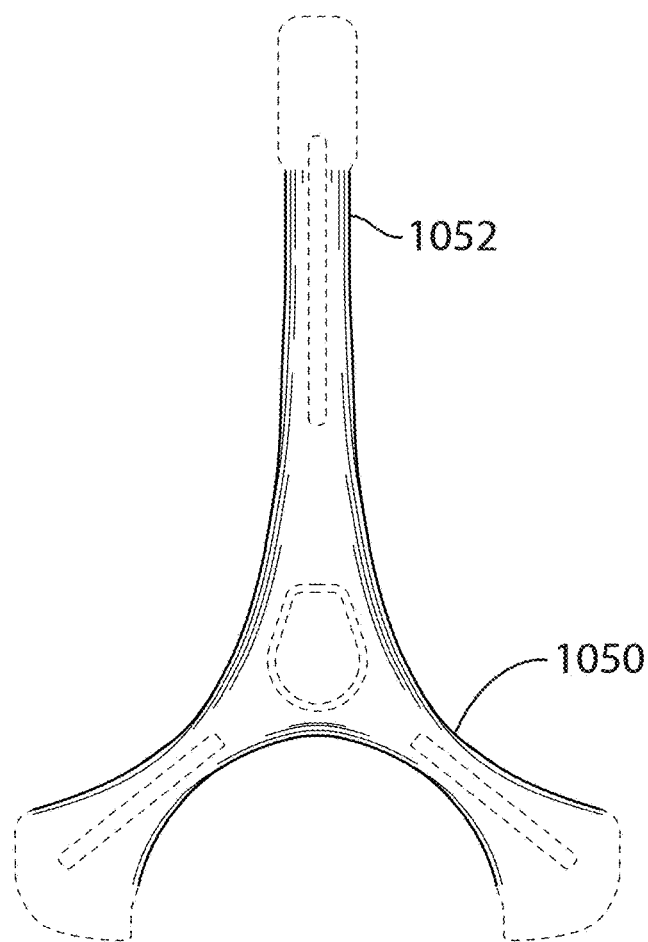
FIG. 17 is a front view of the outwardly projecting portion of FIG. 13.
Figure 18:
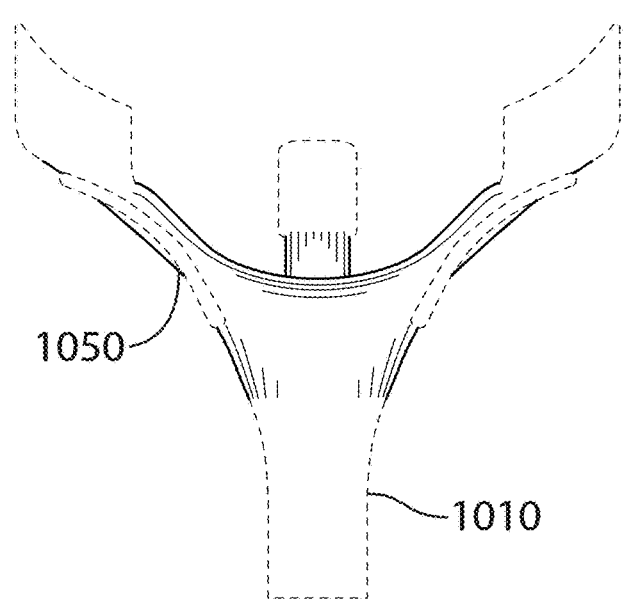
FIG. 18 is a bottom plan view of the outwardly projecting portion of FIG. 13.
Figure 19:
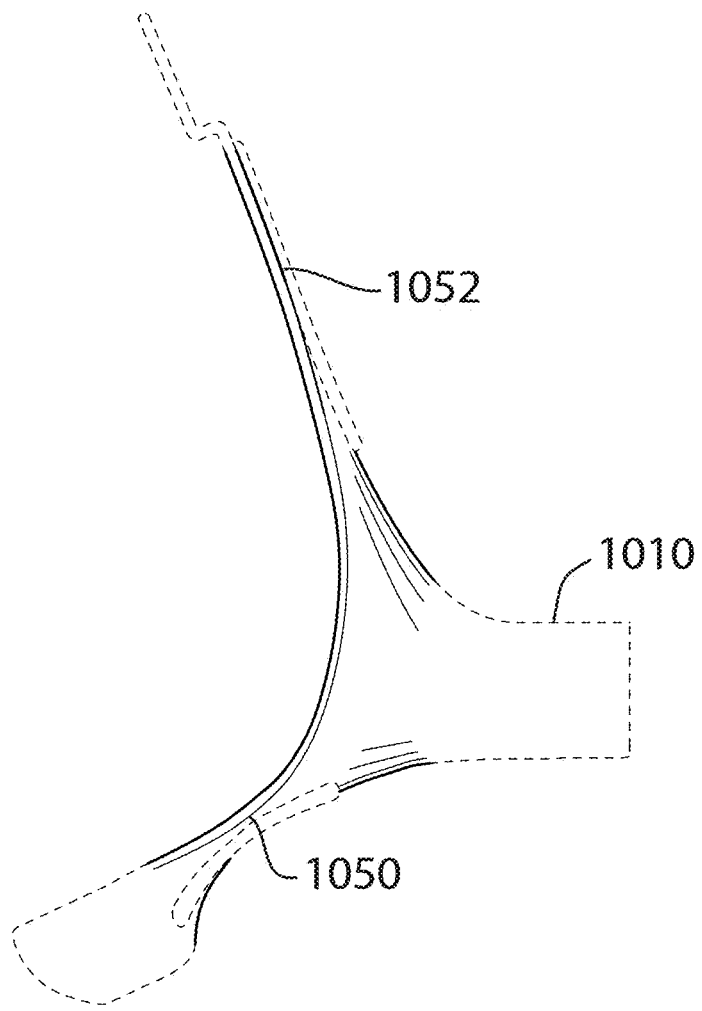
FIG. 19 is a left side view of the outwardly projecting portion of FIG. 13.
Figure 20:
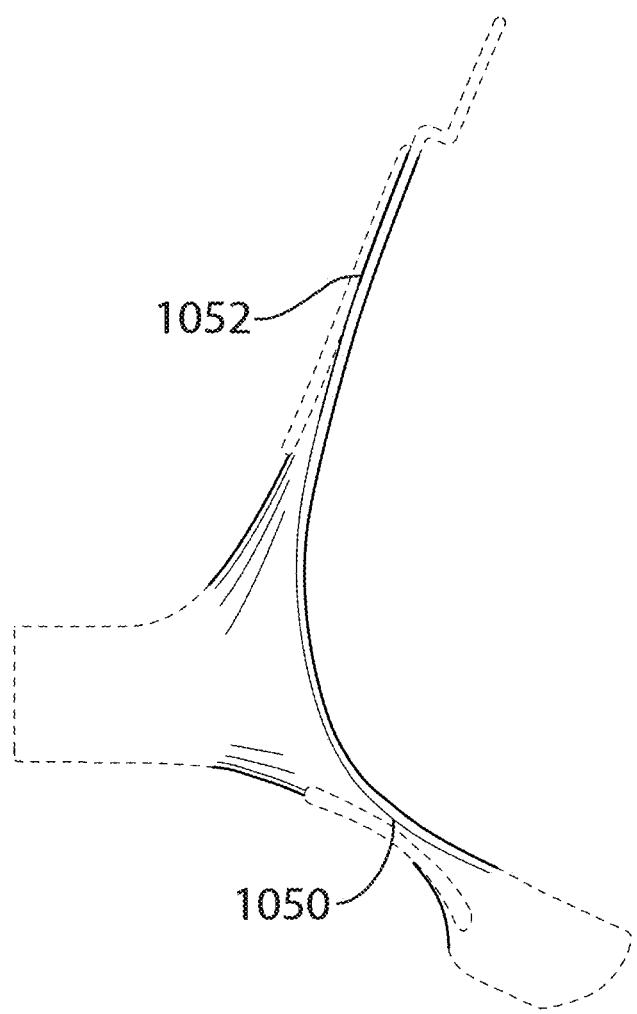
FIG. 20 is a right side view of the outwardly projecting portion of FIG. 13.
Figure 21:
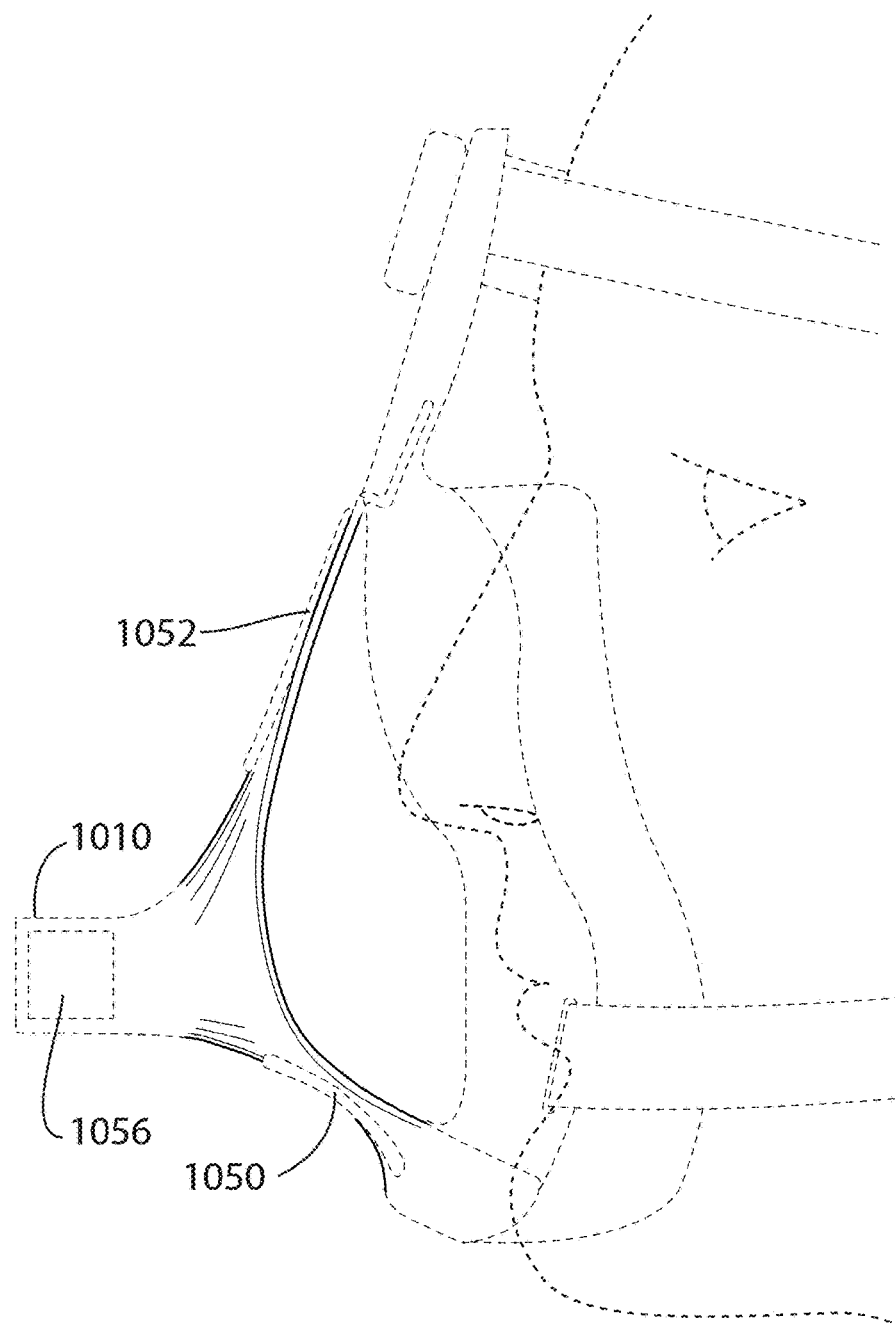
FIG. 21 is a right side view of the outwardly projecting portion of FIG. 13, showing in stippled lines coupling of same to a face resting portion and restraining mechanism of the mask when positioned on the face of a subject, as well as a microphone mounted within a transducer supporting portion of the outwardly projecting portion for capturing sound and airflow produced by the subject while breathing.
Figure 22:
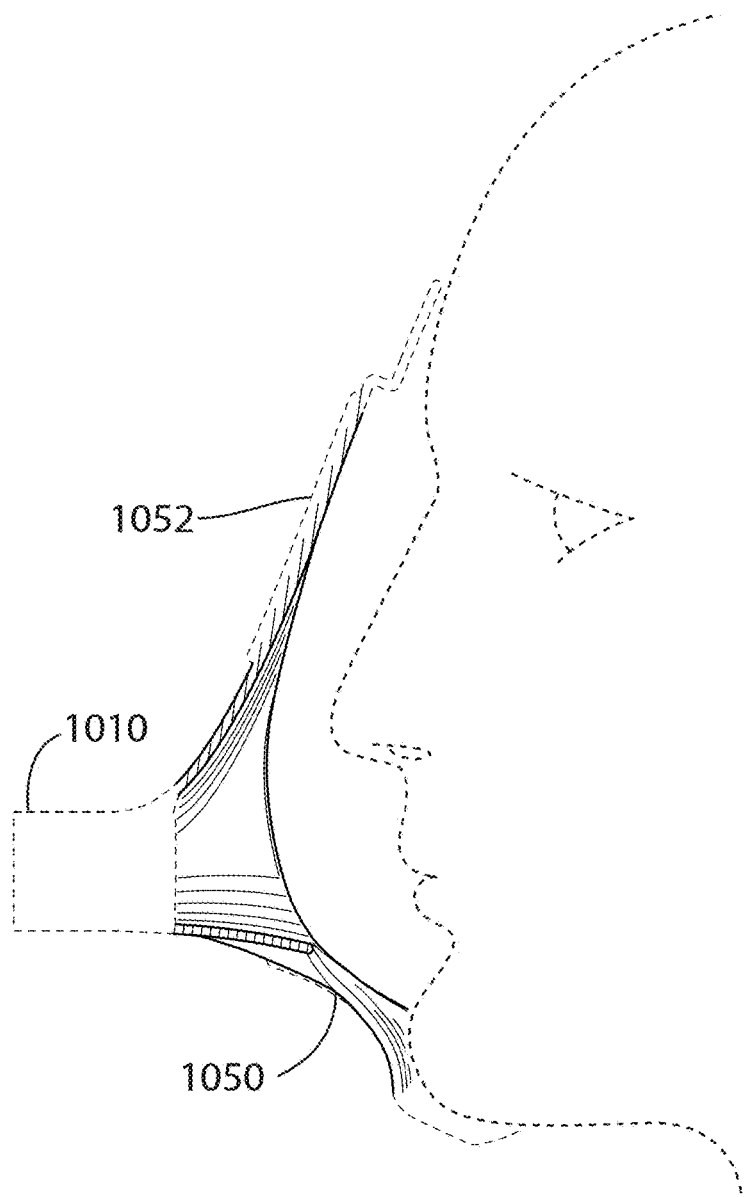
FIG. 22 is a cross section of the outwardly projecting portion of FIG. 13, showing in stippled lines positioning of same on the face of a subject.

Referring now to FIGS. 11 and 12, and in accordance with an illustrative embodiment of the invention, a mask to be worn on a subject's face for use in respiratory monitoring and/or diagnostics will be described. The mask, generally referred to using the numeral 1000, comprises at least one transducer, such as microphones 1002 and 1004 in this example, and a support structure 1006 for supporting same above a nose and mouth area of the subject's face. The support structure 1006 is generally shaped and configured to rest on the subject's face and, in this example, thereby delineate the nose and mouth area thereof (e.g. see FIG. 12), and comprises two or more outwardly projecting limbs 1008 (e.g. three limbs in this example) that, upon positioning the mask 1000, converge into a transducer supporting portion 1010 for supporting microphones 1002 and 1004 at a distance from this area.

Figure 23:
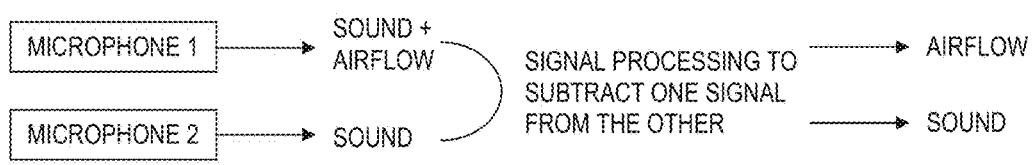
FIG. 23 is a schematic diagram of a process for decoupling a data stream representative of airflow from a combined data stream representative of both airflow and sound, in accordance with one embodiment of the invention.

In general, the at least one transducer is responsive to sound and/or airflow for generating a data signal representative thereof, so to effectively monitor sound and/or airflow produced by the subject while breathing. For example, in the illustrated embodiment, two microphones 1002 and 1004 are provided in the transducer support portion 1010, wherein one of these microphones may be predominantly responsive to sound, whereas the other may be predominantly responsive to airflow. For example, the microphone configured to be predominantly responsive to airflow may be more sensitive to air pressure variations then the other. In addition or alternatively, the microphone configured to be predominantly responsive to sound may be covered with a material that is not porous to air. In addition or alternatively, the microphone configured to be predominantly responsive to sound may be oriented away from the subject's nose and mouth so to reduce an air impact on the diaphragm of this microphone produced by the subject's breathing airflow. In other embodiments, a microphone predominantly responsive to airflow may be positioned in the transducer support portion in line with the subject's nose and mouth, while another microphone may be positioned to the side or on the periphery of the mask to thereby reduce an influence of airflow thereon. In some of these embodiments, the recorded sound from the peripheral microphone, or again from the microphone predominantly responsive to sound, may in fact be used to isolate the airflow signal recorded in the nosepiece, by filtering out the sound signal recorded thereby, for example. An example of this process is schematically depicted in FIG. 23, wherein a sound signal recorded via microphone 2 is used as reference for microphone 1 to further isolate an airflow signal picked up via microphone 1. It will be appreciated that this type of processing may occur locally, via one or more microprocessors disposed directly within the mask, for example, or again via a downstream processing platform, for example implemented at a remotely located diagnostic center.

In yet another embodiment, a single microphone may alternatively be used to capture both sound and airflow, wherein each signal may be distinguished and at least partially isolated via one or more signal processing techniques, for example, wherein a turbulent signal component (e.g. airflow on microphone diaphragm) could be removed from other acoustic signal components (e.g. snoring). Such techniques could include, but are not limited to adaptive filtering, harmonics to noise ratio, removing harmonics from a sound recording, wavelet filtering, etc.

In each of the above examples, the device may be implemented using a single type of transducer, for example one or more microphones which may in fact be identical. It will be appreciated however that other types of transducers, particularly responsive to airflow, may be considered herein without departing from the general scope and nature of the present disclosure. For example, a pressure sensor or airflow monitor may be used instead of a microphone to yield similar results in capturing an airflow produced by the subject while breathing.

Furthermore, while the above examples contemplates the provision of one or more transducers for the recordal of both sound and airflow, it may be desirable, in accordance with other embodiments of the invention, to include only a single transducer for acquiring data representative of only one of sound or airflow. For example, in the illustrative embodiments depicted and described in greater detail below, improved airflow measurements may in fact be used in isolation to provide a certain level of monitoring and diagnosis, without departing from the general scope and nature of the present disclosure.

It will also be appreciated by the skilled artisan that the exact location of the transducer(s)/microphone(s) may, depending on the subject, application and/or further experimentation, be subject to change. For example, the mask may be reconfigured to adjust the position of the at least one transducer, together or independently when considering multiple-transducer embodiments, to be closer to the nose, closer to the mouth, between the nose and mouth, in the upper lip or mustache area of the subject's face, etc. Ultimately, the mask will provide for the ability to capture both sound and airflow, both useful in respiratory monitoring and diagnostics.

Still referring to the embodiment of FIGS. 11 and 12, the support structure further comprises an optional frame 1012 and face resting portion 1014 shaped and configured to contour the face of the subject and at least partially circumscribe the nose and mouth area of the subject's face, thereby facilitating proper positioning of the mask on the subject's face and providing for greater comfort. A restraining mechanism, such as head straps 1016 and 1018, can be used to secure the mask to the subject's face and thereby increase the likelihood that the mask will remain in the proper position and alignment during use, even when the subject is sleeping, for example, in monitoring and diagnosing certain common breathing disorders. It will be appreciated that the mask and diagnostic approaches described below are also applicable, in some conditions, in monitoring and diagnosing a subject's breathing when awake.

In this embodiment, the mask 1000 further comprises a recording device 1020, such as a digital recording device or the like, configured for operative coupling to the at least one transducer, such as microphones 1002 and 1004, such that sound and/or airflow signals generated by the at least one transducer can be captured and stored for further processing. In this particular embodiment, the recording device 1020 is disposed on a frontal member 1022 of the support structure 1006, thereby reducing an obtrusiveness thereof while remaining in close proximity to the at least one transducer so to facilitate signal transfer therefrom for recordal. In providing an integrated recording device, the mask 1000 can effectively be used as a self-contained respiratory monitoring device, wherein data representative of the subject's breathing can be stored locally on the mask and transferred, when convenient, to a remotely located respiratory diagnostic center.

Referring now to FIGS. 13 to 22, the general shape and structural features of support structure 1006, in accordance with one embodiment of the invention, will be described in greater detail. In this embodiment, the support structure comprises three (3) outwardly projecting limbs, namely two opposed limbs 1050 and a central limb 1052, which converge into the transducer supporting portion 1010, thereby forming a tripod-like structure extending from the nose and mouth area of the subject's face when the mask is in position. Each of these limbs has, along at least a portion thereof and in accordance with one embodiment, an inward-facing channel 1054 defined therein for channeling at least a portion of airflow produced by the subject while breathing, toward the at least one transducer disposed within the transducer supporting portion 1010. To further accentuate this feature, the transducer supporting portion 1010 of this particular embodiment is shaped and oriented to further funnel the airflow channeled by the limbs 1050 and 1052 toward the at least one transducer, depicted generically in FIG. 21 as transducer 1056. For instance, the funneling shape may fluidly extend into each of these inward-facing channels 1054 to provide a continuous airflow guide toward the at least one transducer 1056 positioned within the transducer support portion 1010. Furthermore, as will be appreciated by the person of ordinary skill in the art, the provision of limbs 1050 and 1052, as compared to an enclosed mask, provides for reduced airflow resistance, resulting in substantially reduced dead space. As will be appreciated by the skilled artisan, while the limbs and transducer support portion are described as distinct components of the support structure, these terms are merely used herein for the purpose of illustrating a general progression, in this embodiment, of outwardly projecting structures ultimately converging toward one or more adequately supported transducers. Accordingly, while the above describes a substantially funneling transducer support portion, a similar embodiment may rather define a substantially funneling support structure and/or limbs converging to a supported transducer, for example as described in accordance with the following embodiment, and that, without departing from the general scope and nature of the present disclosure.

Figure 25:
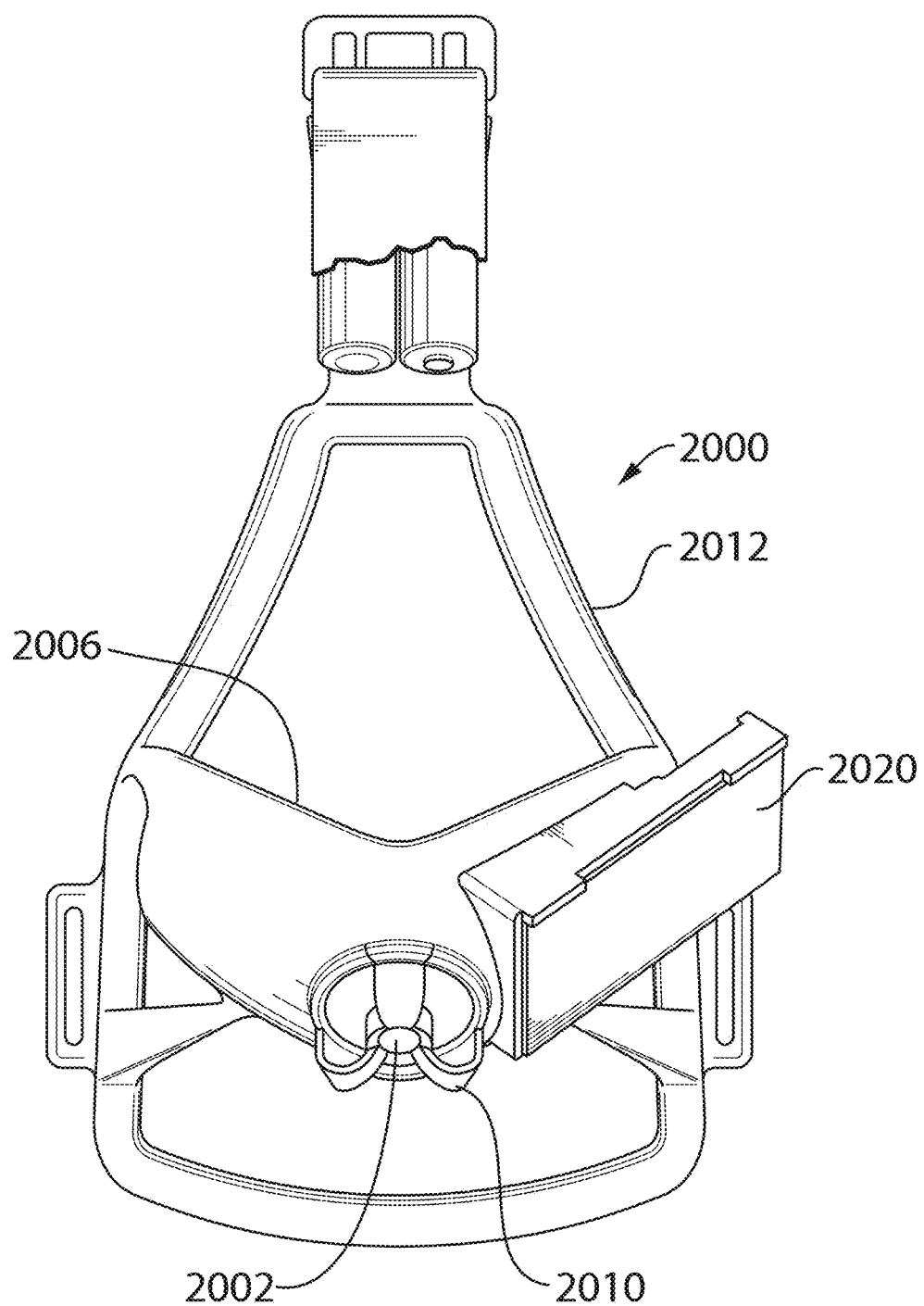
FIG. 25 is a front view of a self-contained mask for use in respiratory monitoring and/or diagnostics, in accordance with one embodiment of the invention.
Figure 26:
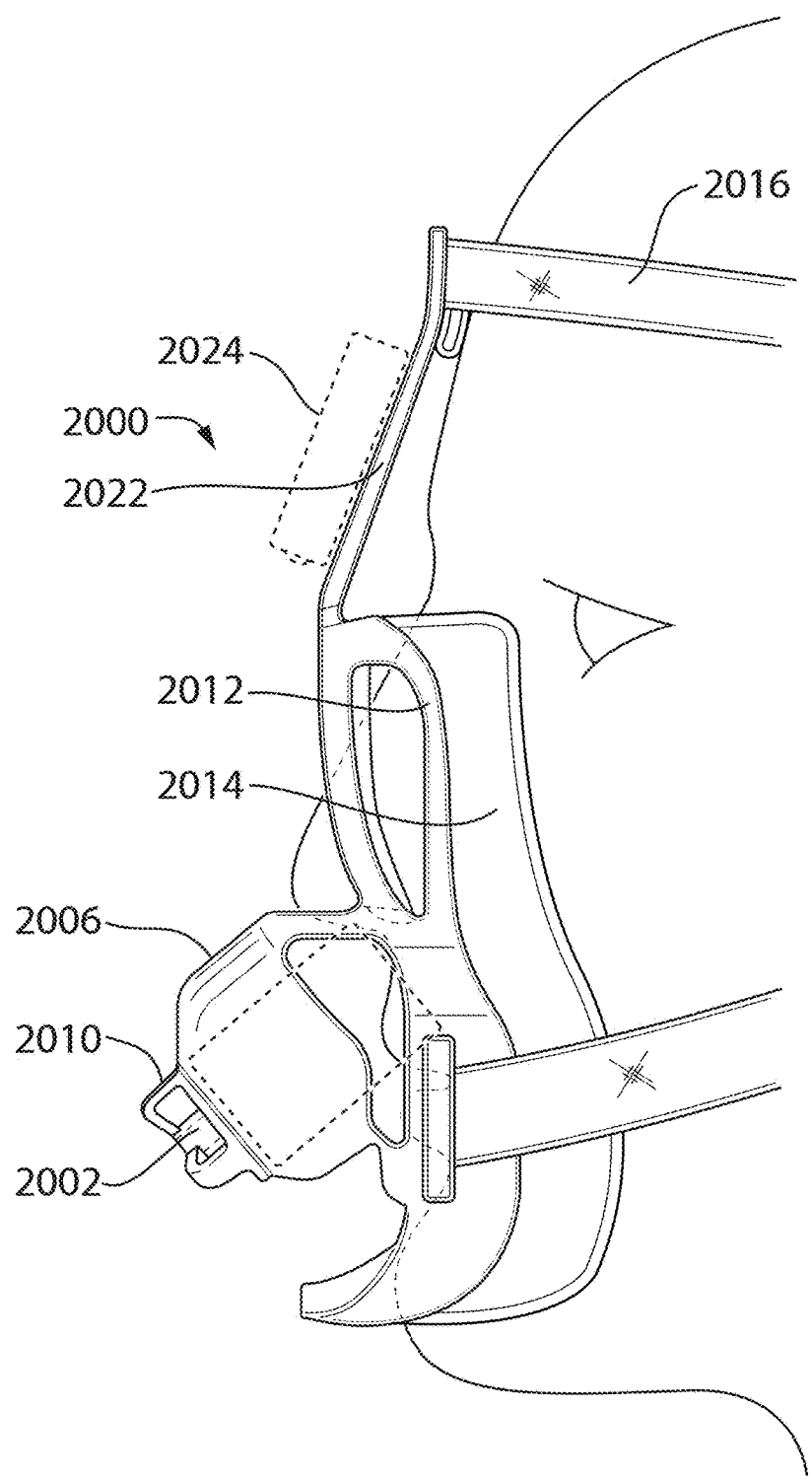
FIG. 26 is a side view of the mask of FIG. 25, as worn on by a candidate's on its face.

Referring now to FIGS. 25 and 26, and in accordance with another illustrative embodiment of the invention, a mask to be worn on a subject's face for use in respiratory monitoring and/or diagnostics will be described. The mask, generally referred to using the numeral 2000, comprises at least one transducer, such as microphone 2002 in this example, and a support structure 2006 for supporting same above a nose and mouth area of the subject's face. The support structure 2006 is generally shaped and configured to rest on the subject's face and extend outwardly therefrom over a nose and mouth area thereof to provide a transducer supporting portion 2010 for supporting the microphone 2002, upon positioning the mask, at a distance from this area.

In this example, the support structure 2006 is shaped and configured to support the transducer 2002 above the nose and mouth area at a preset orientation in relation thereto, wherein the preset orientation may comprise one or more of a preset position and a preset angle to intercept airflow produced by both the subject's nose and mouth.

For example, in one embodiment, the preset orientation may be preset as a function of an estimated intersection between nasal and oral airflow, for example based on an observed or calculated average intersection between such airflows.

For instance, in one embodiment, the preset orientation may comprise a preset position that, upon positioning the mask on the subject's face, is substantially laterally centered relative to the subject's face and longitudinally substantially in line with or below the subject's mouth, thus generally intercepting oral and nasal airflow.

In a same or alternative embodiment, the preset orientation may comprise a preset angle that aligns the microphone, or a principle responsiveness axis thereof, along a line more or less representative of an averaging between general oral and nasal airflows. For instance, in one embodiment, the orientation angle is preset to more or less bisect an angle formed by the transducer's preset position relative to the subject's nose (i.e. nostrils) and mouth. As will be described below, this bisecting angle, which should be construed within the present context to represent an angle more or less directing the transducer's principal responsiveness axis toward a point somewhere between the wearer's nose and mouth, may be determined as a function of measured, observed and/or otherwise estimated nasal and oral breathing patterns, so to improve or enhance the transducer's general responsiveness to airflow originating from the nose and/or mouth of the candidate. Generally, the preset orientation may thus, in accordance with one embodiment of the invention, comprise a preset angle that, upon positioning the mask on the subject's face, substantially aligns the transducer with a point between the subject's nose and mouth.

Figure 27:
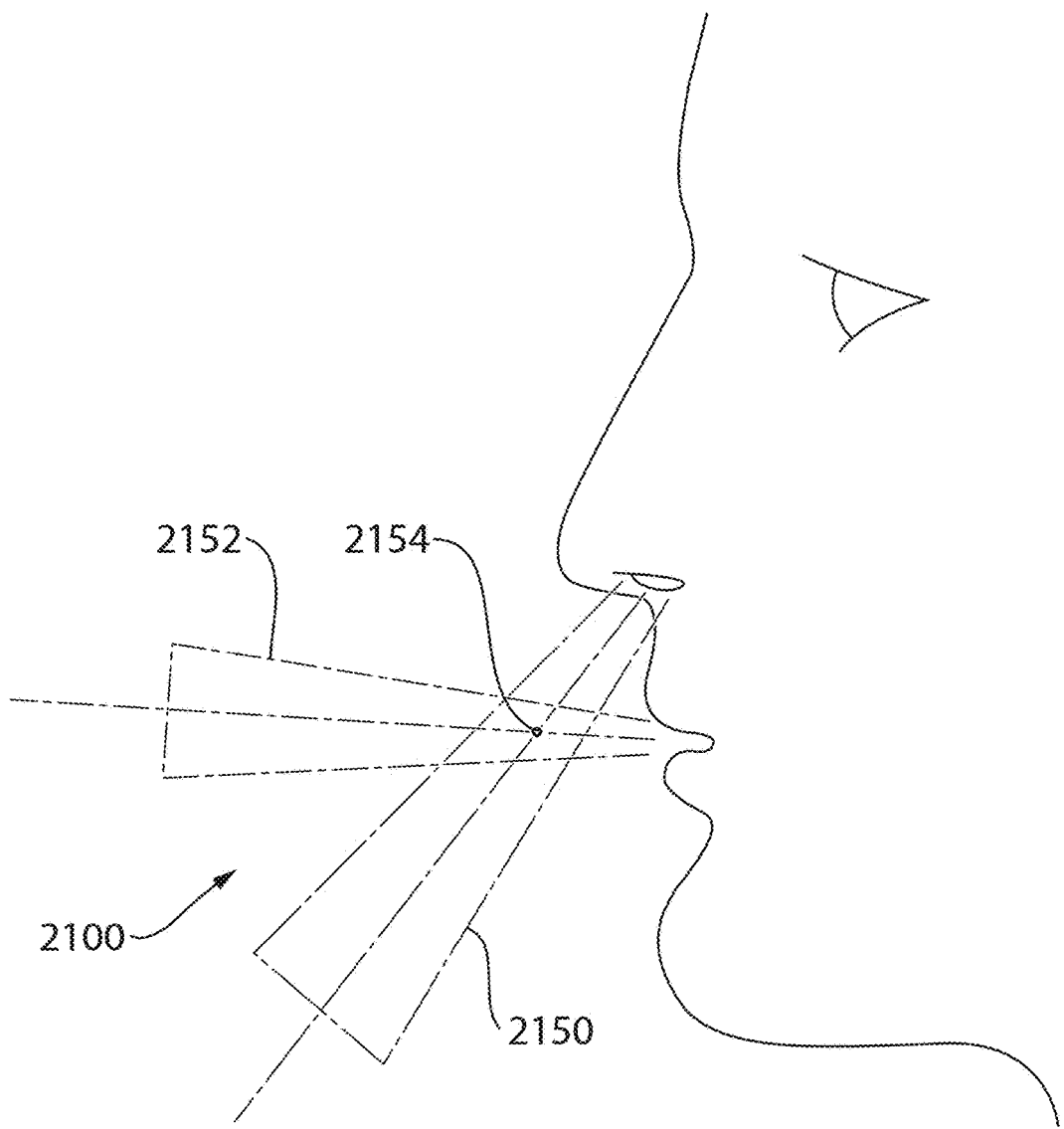
FIG. 27 is a side view diagram of exemplary candidate oral and nasal airflow produced while breathing, in accordance with one embodiment of the invention.
Figure 28:
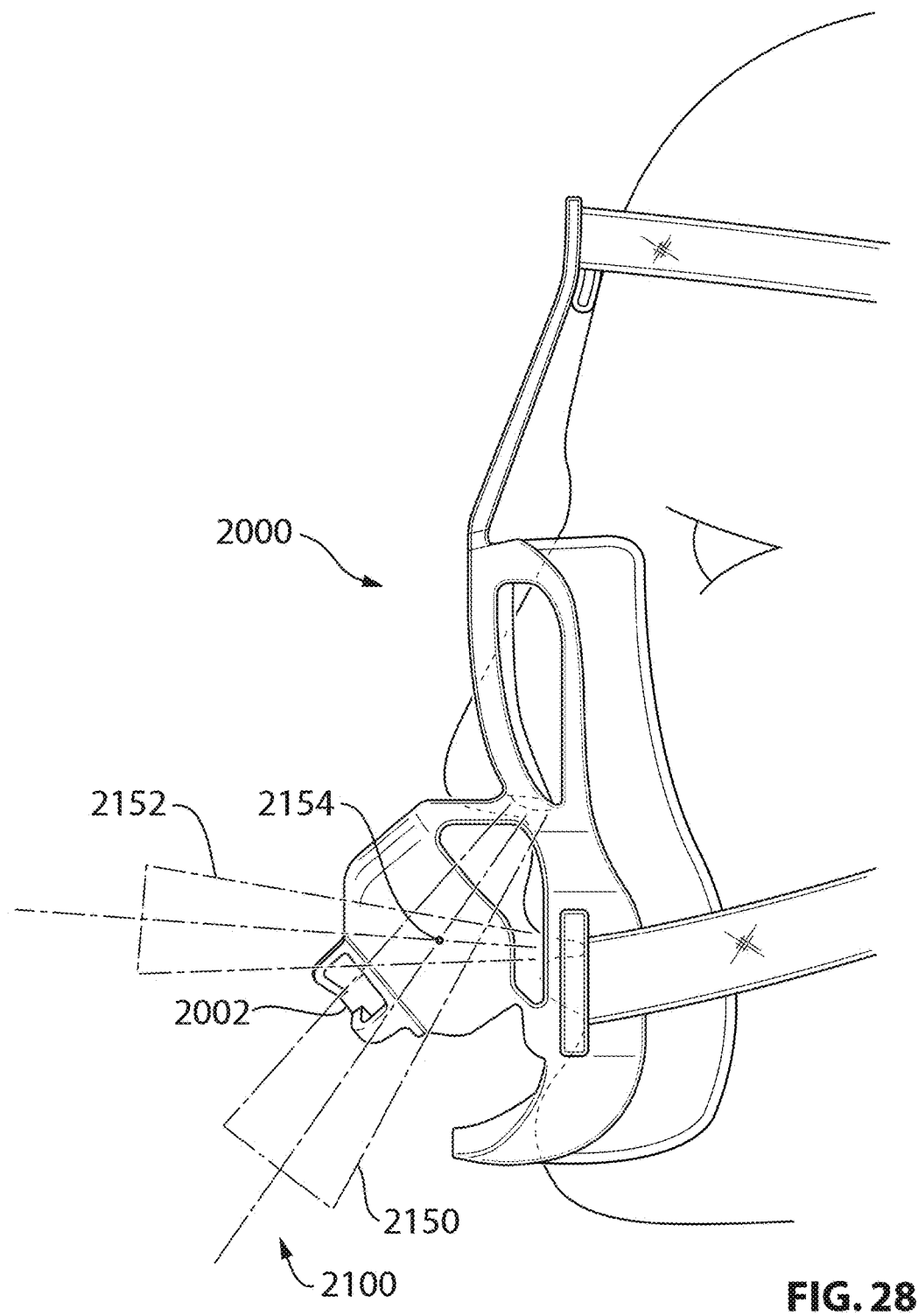
FIG. 28 is a side view of the mask of FIG. 26, showing in dash-dot lines overlapped thereon, the exemplary candidate oral and nasal airflow of FIG. 27 of an estimated candidate oral and nasal airflow, and intersection thereof, in accordance with one embodiment of the invention.

With reference to FIG. 27, an exemplary depiction 2100 of a general nasal (2150) and oral (2152) airflow overlap pattern is shown, in a vertical plane, whereby air directed by either of the nose and mouth is shown to generally spread conically and intersect at a point or in a general intersection area 2154. With reference to FIG. 28, in which the airflow patterns 2100 of FIG. 27 superimpose the mask 2000 of FIG. 27, and in accordance with one embodiment of the invention, the preset orientation of the transducer 2002 is generally selected as a function of the airflow intersection point or area 2154 so to fall in a vicinity thereof, thus effectively improving airflow detection.

Figure 29:
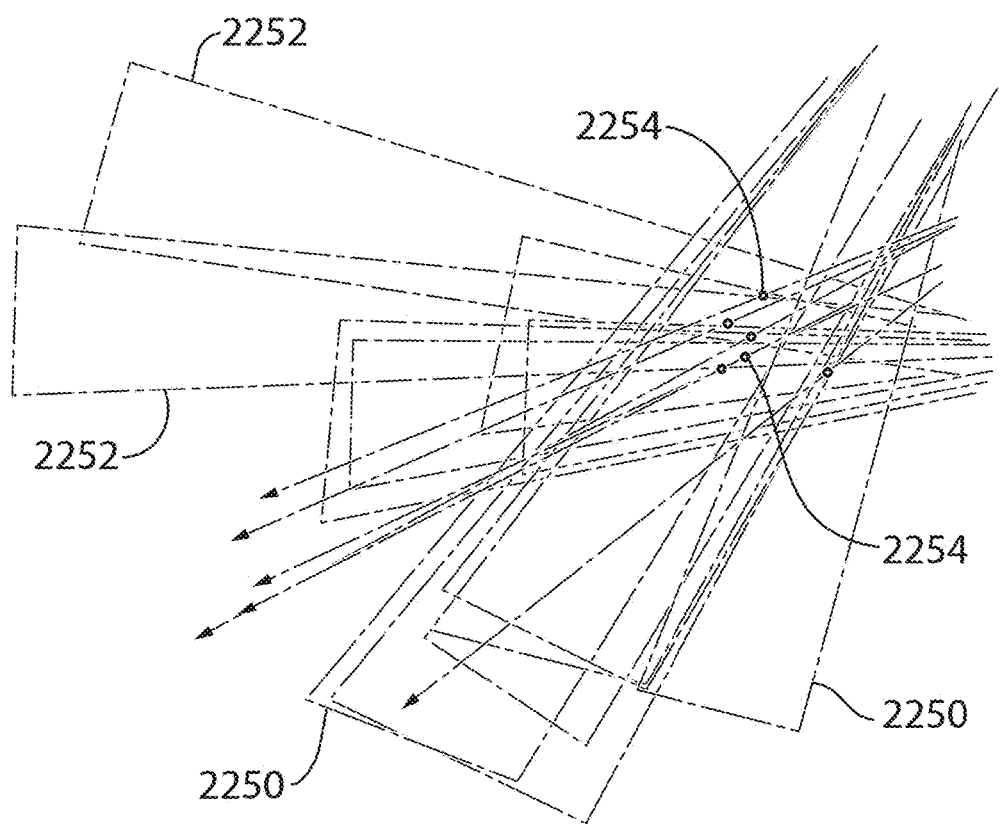
FIG. 29 is a side view diagram of multiple overlapped oral and nasal airflows, and their respective intersections, in accordance with one embodiment of the invention.

In one example, and with reference to FIG. 29, multiple nasal and oral airflow patterns (2250 and 2252, respectively) were traced, and their respective intersections, such as intersection point or area 2254, noted. From these traced patterns and observed intersections, an estimated general intersection point or area could be defined, as a function of which, a preset transducer orientation could then be defined to improve, if not maximized, a responsiveness thereof to nasal and oral airflow produced by different candidates while breathing. As will be appreciated by the skilled artisan, while various observations can be conducted in optimizing transducer orientation in respect of an estimated or anticipated most likely nasal and oral airflow intersection area, other considerations in developing a specific mask design may also affect the ultimate orientation of the transducer. Selecting a preset orientation as a function of such observations, however, may nonetheless improve an overall responsiveness and usability of the mask for breath monitoring and/or diagnostics.

Figure 30:
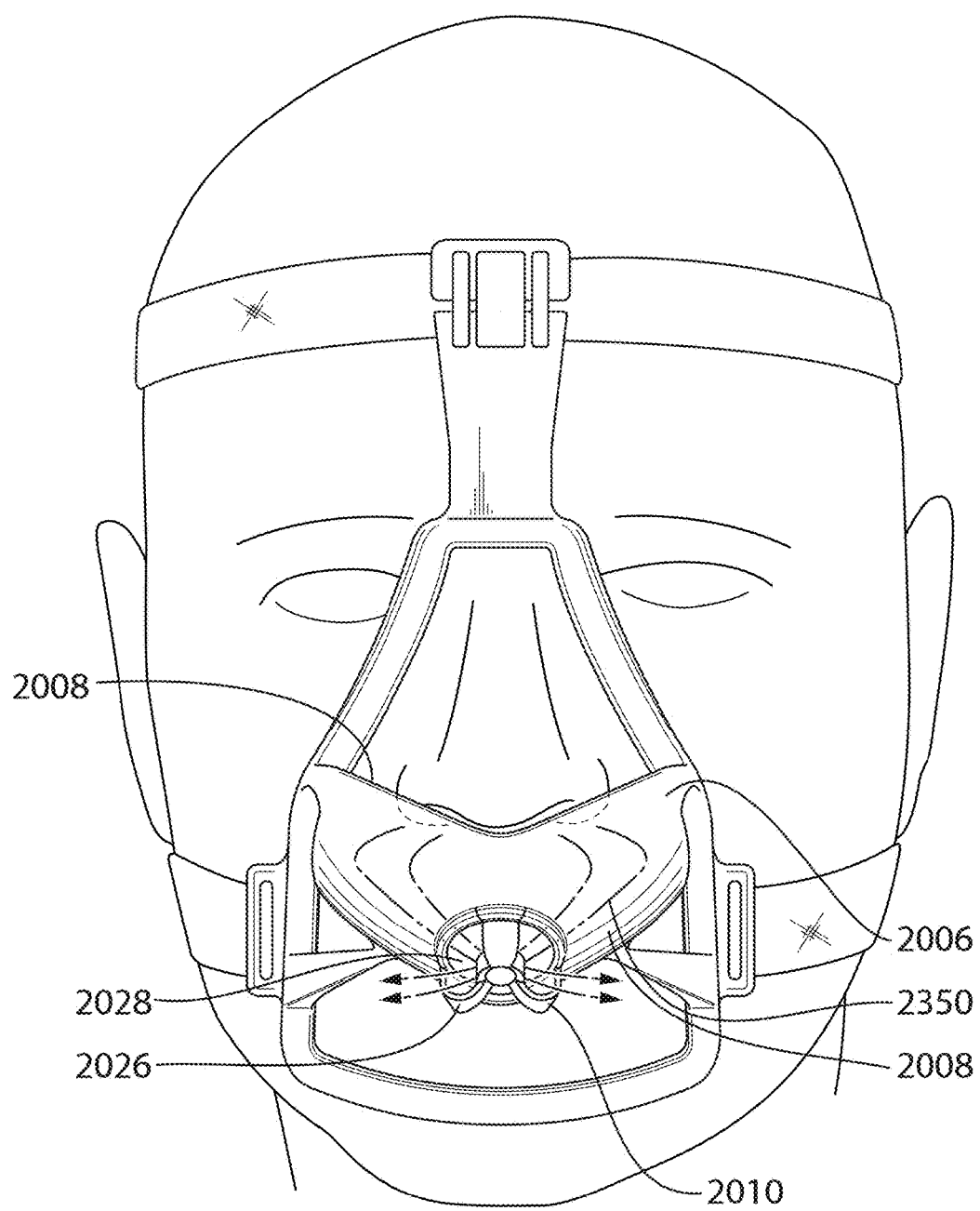
FIGS. 30 and 31 are front and partially cut-away side views respectively of the mask of FIG. 25, showing an illustrative laterally diverging nasal airflow portion being redirected by a funneling shape of the mask, in accordance with one embodiment of the invention.
Figure 31:
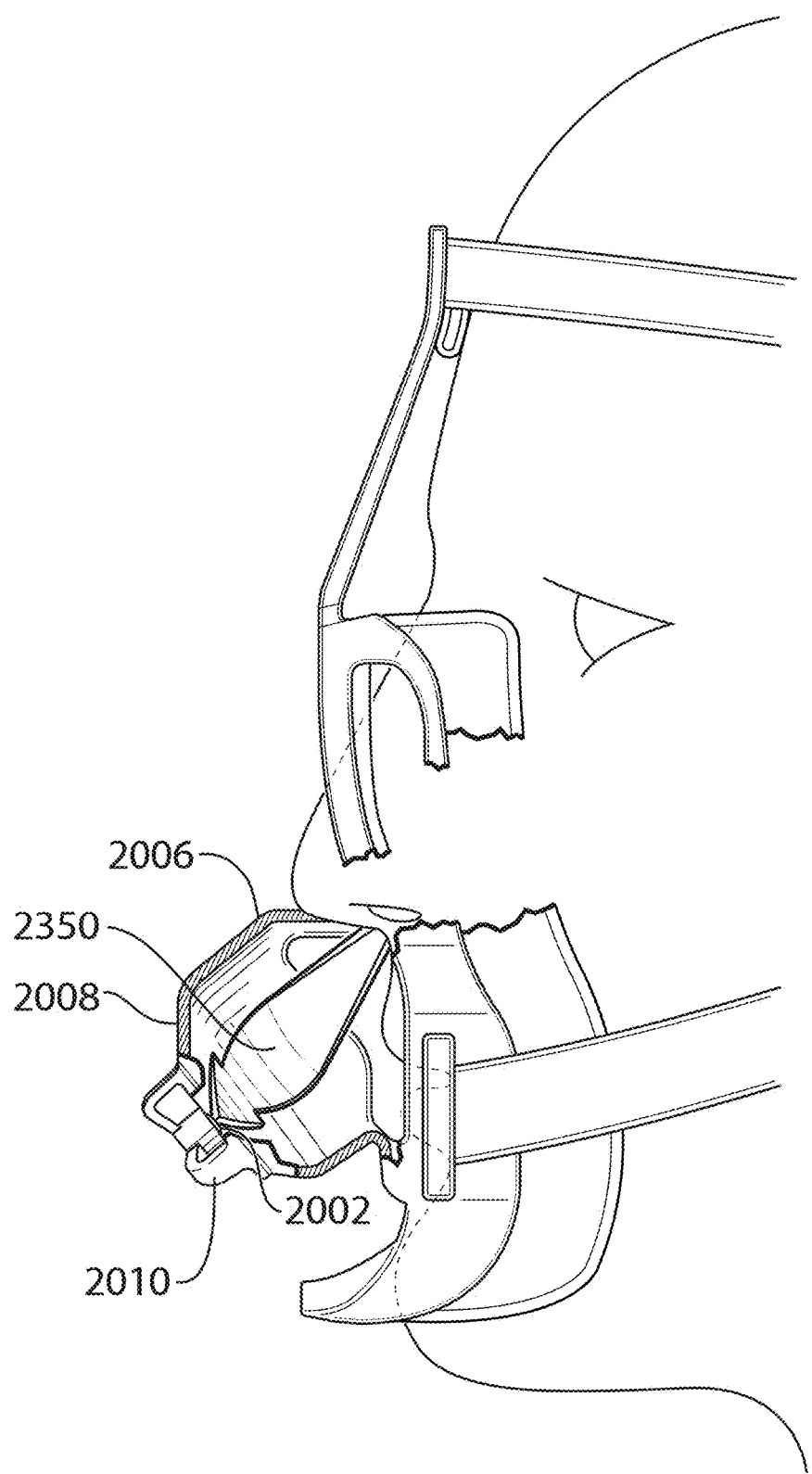

Referring now to FIGS. 30 and 31, the support structure 2006 generally comprises two outwardly projecting limbs 2008 that flow continuously one within the other toward the transducer supporting portion 2010 in defining a funneling shape that substantially converges toward this transducer supporting portion, thus effectively redirecting nasal and/or oral airflow toward the transducer 2002 and allowing for effective monitoring of airflow produced by both the subject's nose and mouth while breathing. As particularly shown in these figures, an illustrative nasal airflow 2350, which will generally more or less diverge laterally from the candidate's nostrils as it is projected more or less obliquely downward therefrom (e.g. as shown in FIGS. 27 to 29), can be effectively collected, at least partially, by the generally concave support structure 2006 to be substantially funneled thereby toward the transducer 2002. Accordingly, in this embodiment, not only is the transducer's preset orientation generally selected as a function of an estimated nasal and oral airflow intersection, the general funneling shape of the support structure 2006 will further redirect at least a portion of laterally diverging nasal (and oral) airflow toward transducer 2002. Similarly, though not explicitly depicted herein, the same generally concave shape of the funneling support structure 2006 will also, partly due to its upwardly titled orientation in this embodiment, also at least partially redirect longitudinally divergent airflow toward the transducer 2002.

With particular reference to FIG. 30, and in accordance with one embodiment, the transducer supporting portion 2010 of the support structure 2006 comprises one or more (three in this embodiment) transducer supporting bridges or limbs 2026 extending from a transducer-surrounding aperture 2028 defined within the support structure 2006. In this embodiment, the provision of bridging limbs 2026 may allow for a general reduction in airflow resistance, which may result in substantially reduced dead space. For example, as schematically illustrated in this Figure, while the general funneling shape of the support structure 2006 allows for a redirection of airflow 2350 toward the transducer 2002, the bridged aperture 2028 allows for this flow of air to continue beyond the transducer 2002, and thereby reduce the likelihood of this flowing air pooling within the mask and/or flowing back onto itself, which could otherwise lead to a generally uncomfortable warm/humid flow of breath back in the candidate's face (and which could thus be breathed in again), and/or lead to unusual flow patterns and/or sounds that could further complicate data processing techniques in accounting for these patterns.

The person of ordinary skill in the art will readily appreciate that while the above describes one example of a particular mask shape and orientation, other shapes and orientations may be exploited to achieve similar results, and that, without departing from the general scope and nature of the present disclosure.

Referring generally to FIGS. 25 and 26, the transducer 2002 is at least responsive to airflow for generating a signal representative thereof, so to effectively monitor airflow, and optionally sound, produced by the subject while breathing. For example, in the illustrated embodiment, a single microphone 2002 is provided in the transducer support portion 2010, wherein both sound and airflow may be recorded, or again, wherein either of these signals may be predominantly recorded based on the application at hand. It will be appreciated that the considerations discussed above with respect to the provision different numbers and/or types of transducers will be readily applicable in the context of this embodiment, as can the single or multiple signal processing techniques discussed above, and their equivalents, be considered in the context of the implementation of this embodiment.

The support structure 2006 further comprises an optional frame 2012 and face resting portion 2014 shaped and configured to contour the face of the subject and at least partially circumscribe the nose and mouth area of the subject's face, thereby facilitating proper positioning of the mask on the subject's face and providing for greater comfort. A restraining mechanism, such as head straps 2016, can be used to secure the mask to the subject's face and thereby increase the likelihood that the mask will remain in the proper position and alignment during use, even when the subject is sleeping, for example, in monitoring and diagnosing certain common breathing disorders. It will be appreciated that the mask and diagnostic approaches described below are also applicable, in some conditions, in monitoring and diagnosing a subject's breathing when awake.

In this embodiment, the mask 2000 further comprises a recording device 2020, such as a digital recording device or the like, configured for operative coupling to the at least one transducer 2002, such that sound and/or airflow signals generated by the at least one transducer can be captured and stored for further processing. In this particular embodiment, the recording device 2020 is disposed on one of the limbs 2008 of the support structure 2006, thereby reducing an obtrusiveness thereof while remaining in close proximity to the at least one transducer so to facilitate signal transfer therefrom for recordal. A battery pack 2024, operatively coupled to the recording device 2020, is provided on a frontal member 2022 of the mask 2000 to power the recording device and transducer in acquiring data free of any external wiring or the like. In providing an integrated and self-supported recording device, the mask 2000 can effectively be used as a self-contained respiratory monitoring device, wherein data representative of the subject's breathing can be stored locally on the mask and transferred, when convenient, to a remotely located respiratory diagnostic center.

As will be appreciated by the person of ordinary skill in the art, the general shape and design of the above-described masks (1000, 2000) can provide, in different embodiments, for an improved responsiveness to airflow produced by the subject while breathing, and that irrespective of whether the subject is breathing through the nose or mouth, predominantly through one or the other, or through both substantially equally. Namely, the ready positioning of an appropriate transducer responsive to airflow relative to the nose and mouth area of the subject's face is provided for by the general spatial configuration of these masks. Accordingly, great improvements in data quality, reliability and reproducibility can be achieved, and that, generally without the assistance or presence of a health care provider, which is generally required with previously known systems.

Furthermore, it will be appreciated that different manufacturing techniques and materials may be considered in manufacturing the above and similar masks, for example as described below, without departing from the general scope and nature of the present disclosure. For example, the entire mask may be molded in a single material, or fashioned together from differently molded or otherwise fabricated parts. For example, the outwardly projecting nosepiece of the mask may comprise one part, to be assembled with the frame and face-resting portion of the mask. Alternatively, the frame and nosepiece may be manufactured of a single part, and fitted to the face-resting portion thereafter. As will be further appreciated, more or less parts may be included in different embodiments of these masks, while still providing similar results. For example, the nose piece, or an equivalent variant thereto, could be manufactured to rest directly on the subject's face, without the need for a substantial frame or face resting portions, as illustrated in the above described embodiments. Alternatively or in addition, different numbers of outwardly projecting limbs (e.g. two, three, four, etc.) or structures may be considered to provide similar results.

As discussed hereinabove, breathing disorders are traditionally monitored and diagnosed using data acquired at sleep centers, where subjects are fitted with a number of electrodes and other potentially invasive monitoring devices, and monitored while they sleep. Clearly, as the subject is both required to sleep in a foreign setting with a number of relatively invasive and obtrusive monitoring devices attached to them, the data collected can often be misleading, if the subject even ever manages to get any sleep to produce relevant data. Clearly, other respiratory monitoring and diagnostic approaches can be implemented while the subject is awake, and such approaches are fully within the realm of the present disclosure as the masks and methods disclosed herein may, in some embodiments, be rendered equally useful in monitoring or diagnosing sleeping and awake subjects.

Figure 24:
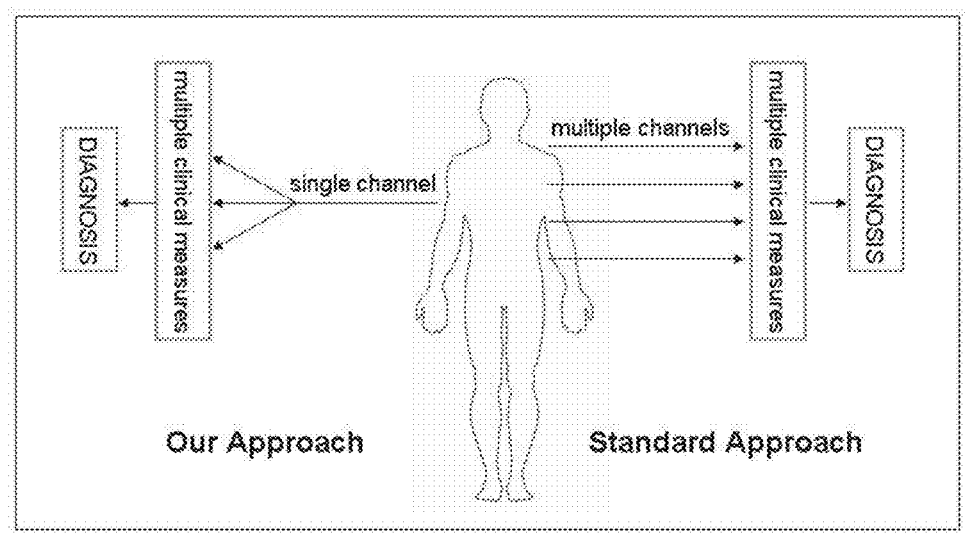
FIG. 24 is a schematic diagram comparing a standard respiratory diagnosis approach with a respiratory diagnostic method in accordance with one embodiment of the invention.

Furthermore, known respiratory diagnostic systems, for example as depicted in FIG. 24, generally require the acquisition of multiple sensory data streams to produce workable results that may include breath sounds, airflow, chest movements, esophageal pressure, heart rate, etc. Similarly, known portable monitoring devices proposed for the diagnosis of sleep apnea generally require subjects to adequately position and attach several wired electrodes responsive to a number of different biological parameters, such as listed above, which generally reduces the comfort and compliance of subjects and increases chances of detachment and/or displacement of the electrodes. Given that portable sleep apnea monitors are used in the absence of an attending health care professional, inaccurate placement or displacement of electrodes cannot be easily detected until the data is transferred to the health center. On the other hand, simplified portable respiratory monitoring devices, as discussed above, only produce data with respect to either airflow or sounds generated during breathing, which limited data sets are generally insufficient in adequate respiratory disorder diagnostics.

In comparison, the respiratory monitoring and/or diagnostic masks described above in accordance with different embodiments of the invention may provide a number of advantages over known techniques. For example, all elements of these self-contained diagnostic masks are contained in a single unit including for instance, the at least one transducer, power supply, electronics, and data storage. The at least one transducer is embedded within the mask structure and thus readily positioned on the subject's face by the very nature of the mask's spatial configuration. Accordingly, proper positioning is generally guaranteed, allowing for adequate capture of both sound and/or airflow produced by the subject while breathing, while reducing the number of required electrodes. Furthermore, as all wiring and circuitry may be embedded within these masks, problems traditionally associated with disconnection of sensory electrodes are practically eliminated. The subject is also free of external wiring, thereby reducing subject discomfort and increasing compliance. This advantage is diagrammatically illustrated in FIG. 24, wherein a single physical data channel can be produced locally using a self-contained mask, and communicated to a diagnostic center where signal processing, for example as described below, enables extraction of a number of clinical measures useful in providing similar diagnostics as that only previously available using multiple electrodes in conventional systems. It will be appreciated that reducing the number of physical channels provides great advantage in deploying a portable device wherein a layman is required to wear the device in the absence of a trained health care provider. In the present diagram, it will be appreciated that reference to a "single channel" in fact generally represents a single physical link between the subject, and what could ultimately result in a full respiratory diagnosis. Namely, the subject in this embodiment is only requested to wear a mask which allows for recordal of sound and/or airflow via one or more transducers, while allowing for the downstream processing of multiple clinical measures from this single data acquisition device type. To the contrary, clinical and known portable devices generally require multiple data outputs provided by a multiplicity of data acquisition devices and types so to access multiple clinical measures, which, as discussed above, reduces subject comfort and compliance, and may therefore reduce data reliability and reproducibility.

The alternative in the art, is to reduce data acquisition to a single measure, which, in general, has limited value.

In one embodiment, the recorded data is stored, and optionally encrypted on a removable data storage device, such as an SD card or the like. For example, analog data acquired by the one or more transducers can be locally pre-amplified, converted into digital data (e.g. via a local A/D converter) and stored in the removable memory device. The stored data can then either be uploaded from the memory card to a local computing device (e.g. laptop, desktop, palmtop, smartphone, etc.) for transmittal to a remotely located diagnostic center via one or more wired and/or wireless communication networks, or physically shipped or delivered to the remotely located diagnostic center for processing. Namely, the acquired data can be processed via one or more diagnostic software platforms, or the like (e.g. as discussed hereinbelow), to evaluate the subject's breathing and provide, as appropriate, diagnosis of relevant breathing disorders. Furthermore, given this system's generally distributed architecture, various distinct and/or complimentary processing techniques and algorithms may be applied to a same data set to increase diagnostic complexity and/or reliability, for example. In such embodiments, given that the data storage device retains all relevant data, once the data is shipped, the mask itself may be disposed of, or again, reused by the same subject to acquire further data in respect of a same or similar breathing study.

It will be appreciated that different types of data transfer and communication techniques may be implemented within the present context without departing from the general scope and nature of the present disclosure. For example, while the above examples contemplate the use of a digital recording device having a removable data storage medium, such as a memory card of the like, alternative techniques may also be considered. For example, the recording device may rather include a wireless communication interface wherein data integrally recorded thereon can be wirelessly uploaded to a computing device in close proximity thereto. For example, Wi-Fi or Bluetooth applications may be leveraged in transferring the data for downstream use. Alternatively, the device may include a communication port wherein recorded data may be selectively uploaded via a removable communication cable, such as a USB cable or the like. In yet another example, the recording device itself may be removably coupled to the mask and provided with a direct communication interface, such as a USB port or the like for direct coupling to an external computing device. These and other such examples are well within the realm of the present disclosure and therefore, should not, nor should their equivalents, be considered to extend beyond the scope of the present disclosure.

As will be appreciated from the proposed diagnostic procedures described below, the provision of a respiratory monitoring and diagnostic mask, as described herein, provides for the implementation of a method for remotely diagnosing a breathing disorder of a subject. Namely, upon providing the subject access to a self-contained mask, as described herein, the subject may then proceed to wear the mask, when appropriate for the condition to be monitored, and integrally record sound and/or airflow produced during breathing. Once this data is transferred to a remotely located diagnostic center, a breathing disorder may be diagnosed on the basis of the processed sound and/or airflow signals recorded by the mask. Namely, no additional sensors or recordings are required to achieve workable results, leaving the subject to conduct all relevant recordings at home, if so desired, remote from any qualified health care practitioner. Furthermore, the general improvements in transducer positioning achieved by the design of the various embodiments of the masks described herein, allow for greater data reliability and reproducibility, while significantly reducing discomforts or inconveniences to the subject.

Figure 2A:
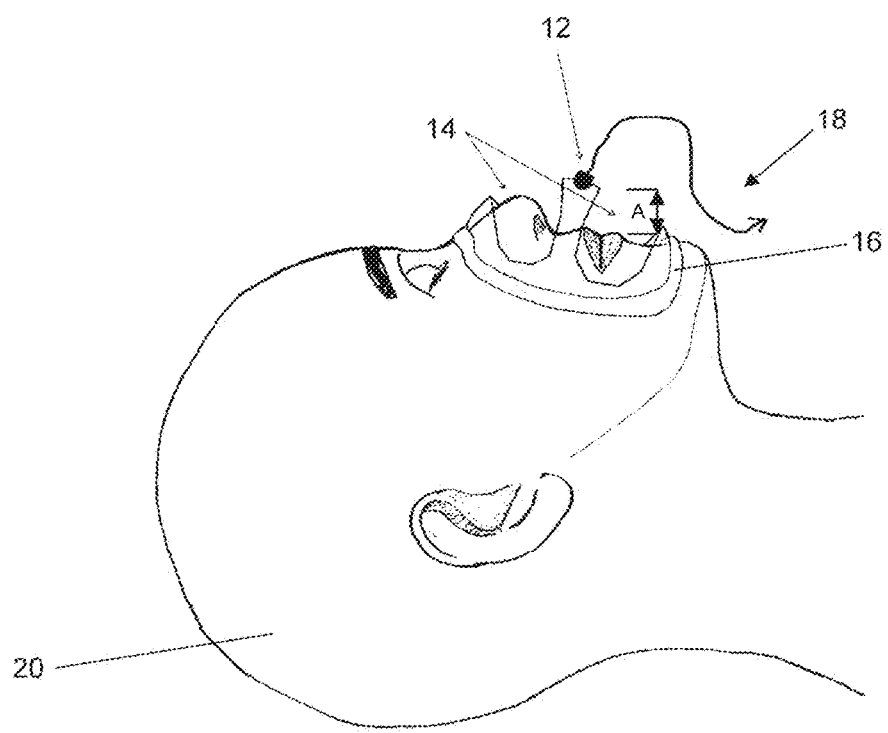
FIG. 2a is side view of an exemplary embodiment of a microphone and transducer set-up on an individual wherein the microphone is attached to a face mask located on the front of an individual's face.
Figure 2B:
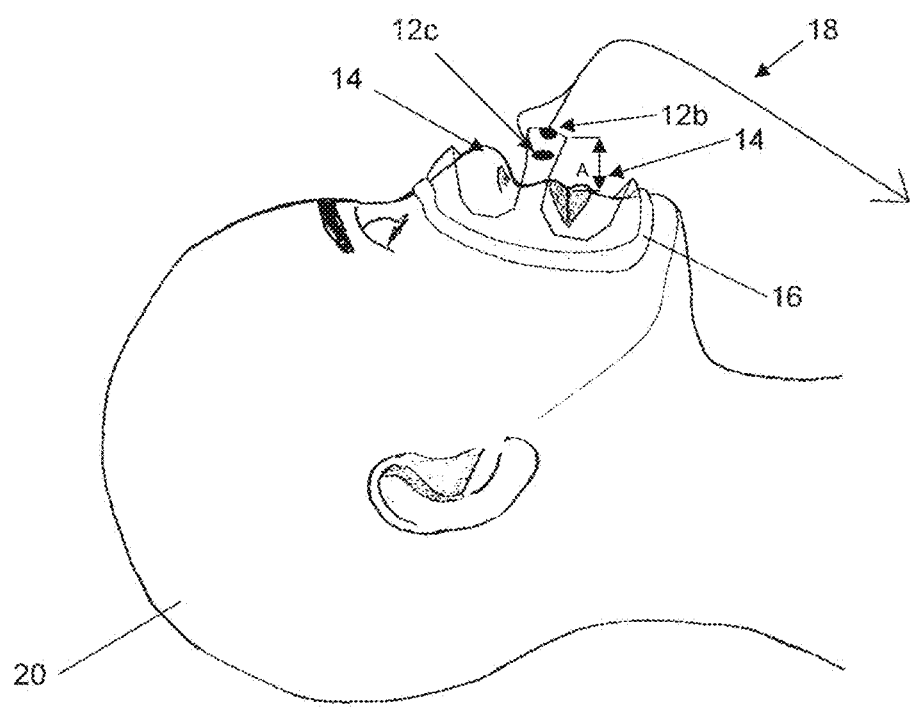
FIG. 2b is side view of an exemplary embodiment of a 2-microphone and transducer set-up on an individual wherein the microphones are attached to a face mask located on the front of an individual's face.

In accordance with another embodiment, a microphone 12 is located in a position proximal to an individual's mouth as shown in FIGS. 2a and 2b, in this case by a dimension A of approximately 3 cm in front of the individual's face, i.e. at a distance from a nose and mouth area of the subject's face. The microphone 12 may be configured to communicate with the microprocessor by way of an interface or other data acquisition system, via a signal transducing link or data path 18 to provide one or more data collection modules with the microphone 12. Thus, such data collection modules and the microphone are operable to collect breathing sounds emanating from the individual's mouth and nose, during the inspiration and/or expiration phases of breathing. For example, an exemplary microphone response curve is shown in FIG. 1. The acoustic signal data breathing sounds collected from the individual may be comprised of both airflow sounds from the individual's breathing applying air pressure to the microphone diaphragm and actual breathing sounds resultant from the individual's breathing being recorded and/or collected by the microphone 12. Furthermore, the acoustic signal data breathing sounds collected from the individual may be, in another exemplary embodiment, comprised of substantially only actual sounds resultant from the individual's breathing being recorded and/or collected by the microphone 12. In still yet another embodiment, the acoustic signal data breathing sounds collected from the individual may be comprised of substantially only airflow sounds resultant from the individual's breathing applying air pressure to the microphone diaphragm and being recorded and/or collected by the microphone 12. As used herein, term "airflow sounds" refers to the air pressure resultant from an individual's breathing being applied to and causing the microphone's diaphragm to move such that the microphone collects and produces data for the audio recording.

The microphone 12, for example, may be coupled in or to a loose fitting full face mask 16 as shown in FIGS. 2a and 2b. Furthermore, the face mask 16 may include at least one opening 14 to allow for ease of breathing of an individual 20. For example, the microphone 12 may be in a fixed location with a spacing of dimension "A", of about 3 cm in front of the individual's face as shown schematically in FIG. 2a; however other distances in front of the individual's face may be desirable in some embodiments. The microphone 12, in this case, is embedded in a respiratory mask 16 which is modified by cutting away material so as produce opening 14 such that only a structural frame portion remains to keep the microphone 12 in a fixed location relative the nostrils and the mouth of an individual 20. In one example, the audio signals from the microphone may be digitized using an audio signal digitizing module and digitized sound data to be transferred via transducing link 18 to the computer using a USB preamplifier and audio interface (M-Audio, Model Fast Track Pro USB) with a sampling rate of 22,050 Hz and resolution of 16 bits. Although various types of audio interfaces may be used, in the instant exemplary embodiment, an external audio interface provides suitable results over the other types of audio adapters, for example, built-in audio adapters due to the superior signal to noise (S/N) ratio of the external adaptor which is about 60 dB at 1 kHz. Sound recordings may then be passed through a $4^{th}$ order band-stop digital filter with a centre frequency of about 60 Hz to suppress line interference. Other structures may also be used to locate the microphone in position, as including support structures positioned against a plurality of locations on the individual or stationed adjacent the individual as required.

Furthermore, in another exemplary embodiment, a two microphone system may be useful. In such a system, as shown in FIG. 2b, one of the microphones, a first microphone 12b, may be configured to collect actual breathing sounds and airflow sounds whereas the other microphone, a second microphone 12c may be configured to collect substantially only actual breathing sounds. In this embodiment, the waveform sounds and/or data collected from the second microphone 12c may be subtracted or filtered from the waveform sounds collected from the first microphone 12b, thereby resulting in a waveform data stream of substantially only airflow sounds. The airflow sounds may be resultant of pressure air from an individual's breathing being collected as applied to the diaphragm of a microphone as noted above. Subsequently, the airflow sounds may then be used as a waveform amplitude acoustic data stream in accordance with the forgoing method.

Figure 5:
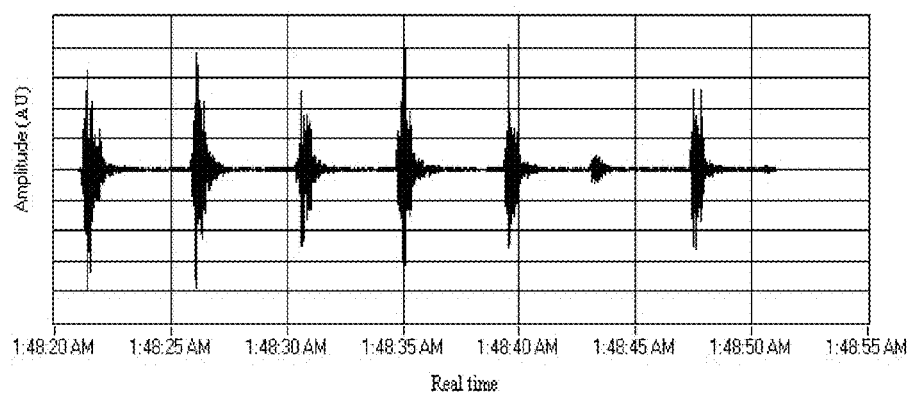
FIG. 5 is a digitized raw data wave plot representative of breathing sound amplitude versus time.

A raw acoustic data stream of breathing sounds, as shown in a representative plot, for example in FIG. 5, is then collected for each of a plurality of respiratory phases to form a bioacoustics signal recording, wherein the acoustic data stream is subsequently transformed.

As will be described below, in at least one embodiment, a method and an apparatus are provided to monitor, identify and determine the inspiratory and/or expiratory phases of the respiratory cycle of an individual 20 from the frequency characteristics breathing sounds. It is understood that a numerical comparative analysis of the frequency spectrum as transformed from waveform amplitude data of breathing sounds and/or airflow sounds of an individual 20 may be useful to differentiate between the inspiration and expiration phases of breathing.

It will be appreciated by the person of ordinary skill in the art that while the below example describes a method in which a mask as depicted in FIGS. 2a and 2b was used for data acquisition and breath monitoring/diagnostics, a mask as described above with reference to FIGS. 11 to 22, or with reference to FIGS. 26 and 27, could also be used to produce similar effects, and that, without departing from the general scope and nature of the present disclosure. Furthermore, while the below predominantly proposes a wired solution for real-time monitoring, a similar approach may be applied, for example with respect to a self-contained mask as described above, wherein processing steps applied to the locally acquired data could be implemented remotely at an appropriate diagnostic center.

It will also be appreciated that while the below description provides one example of a breath monitoring application of the herein-described masks, other similar or distinct breath monitoring and/or diagnostic approaches may be applied using the data acquired via different embodiments of these masks, and that, without departing from the general scope and nature of the present disclosure. For example, different monitoring and/or diagnostic methods relying on breath sound and/or airflow measurements may be implemented with and rely on data acquired using different mask embodiments as described herein, which studies may include, but are not limited to, sleep disorders such as apneas and/or hypopneas, breathing disorders, snoring, and other such conditions as will be readily apparent to the person of ordinary skill in the art. Accordingly, the below example should not be construed as limiting to the above embodiments, but rather as a means to exemplify it's possible utility within a particular context.

Data Acquisition

Data were collected from 10 consecutive men and women at least 18 years of age referred for overnight polysomnography (PSG). The subjects' characteristics are shown in Table 1. Breath sounds were recorded by a cardoid condenser microphone (Audi-Technica condenser microphone, Model PRO 35x). The microphone's cardioid polar pattern reduces pickup of sounds from the sides and rear, improving isolation of the sound source. The microphone 12 used for recording breath sounds has a relatively flat frequency response up to 2000 Hz as shown in FIG. 1. Furthermore, the microphone 12, as used herein has a higher output when sound is perpendicular to the microphone's diaphragm as shown by the solid line in FIG. 1, which helps reduce low frequency ambient noise interference. In this example, the microphone 12 was embedded in the centre of a loose fitting full face mask 16 modified to reduce airflow resistance and eliminate dead space by way of large openings 14 as shown in FIGS. 2a and 2b. The microphone 12 attached to the face mask 16, and was located in front of the individual's face. The mask 16 provides a structural frame portion to keep the microphone in a fixed location, at a dimension A of approximately 3 cm in front of the individual's face, so as to record breathing sounds to an audio recording device, such as a computer as described above, to make an audio recording thereof. In some exemplary embodiments, the audio recording of breathing sounds may be made and recorded in analog format prior to digitizing the audio recording. However, in other embodiments the audio recording of breathing sounds may be digitized in real-time. Furthermore, in some exemplary embodiments, the processing of the audibly recorded waveform data or acoustic signal data may be performed in real-time, so as to provide substantially instantaneous information regarding an individual's breathing. In an exemplary embodiment, digitized sound data were transferred to a computer using a USB preamplifier and audio interface (M-Audio, Model MobilePre USB) with a sampling rate of 22,050 Hz and resolution of 16 bits. Although various types of audio interfaces may be used, in the instant exemplary embodiment, an external audio interface was preferred over a built-in audio adapter due to the better signal to noise (S/N) ratio of the external audio interface, which was 91 dB. FIG. 5 shows a 25-second waveform amplitude recording plot. However, in other exemplary embodiments, it may be desirable to record breathing sounds for a time period of from about 10 seconds to 8 hours. In some exemplary embodiments it may be desirable to record breathing sounds for a time period of from about 10 second to about 20 minutes. In other exemplary embodiments, it may be desirable to record breathing sounds for greater than 20 minutes.

Breathing Acoustics Analysis

In an exemplary embodiment, full night breath sound recordings were displayed on a computer screen similar to the computer screen 1.2 of FIG. 3. A representative raw acoustic data waveform plot, as may be shown on a computer screen 1.2, is provided in FIG. 5 for a 25-second recording. Each increase in amplitude represents a single breath. The individual phases of a breathing cycle are not readily resolvable in FIG. 5 owing to the time scale being too large to resolve single breath details. For example, FIG. 7a more clearly shows the inspiration and expiration phases of a breathing cycle in a waveform amplitude versus time plot. The recordings were visually scanned to identify periods of regular breathing. After visual scanning, the recordings were played back for auditory analysis.

Sequences of normal breaths that did not have signs of obstructive breathing such as snoring and interruptions, or other irregularities such as tachypnea (rapid breathing), or hyperventilation (deep breathing) were then included in the subsequent frequency analysis. However, snoring and other types of noisy breathing can also be included in this analysis by applying a pre-processing technique that isolates turbulent from non-turbulent components, (e.g. as shown in FIG. 23) whereby ultimately, the turbulent component may be selected for further processing. This process was repeated to select three random parts of an individual's sleep. If a portion of the recording fulfilled the aforementioned inclusion criteria, then 3 to 4 consecutive breaths were selected from that portion. A total of 10 breaths were selected from each individual. During the process of selecting the individual's breathing sound portions, the investigator did not have a previous knowledge of the sleep stage. Therefore, the investigator was blind to the sleep stage of an individual while selecting the analyzed breaths except for knowing that sampling started after the onset of sleep. The real-time stamp of each breath was registered in order to retrieve the sleep stage in which it took place in afterwards. Subsequently, the investigator listened to these breathing sounds again to divide each breath into its inspiratory, expiratory and interbreath phases. Each phase was labeled manually.

The data array of each breathing phase was passed through a hamming window and a 2048-point Fast Fourier Transform (FFT) of the windowed data with 50% overlap was calculated. The resultant frequency spectrum was displayed on a computer screen for visual analysis. The frequency spectra of the interbreath pauses were also calculated and incorporated in the analysis to control for the effect of ambient noise. Careful visual examination of spectra revealed that during inspiration, the amplitude of signals above 400 Hz was consistently higher than during expiration. Therefore, it was determined that the bands ratio (BR) of frequency magnitude between 400 to 1000 Hz, to frequency magnitude between 10 to 400 Hz is higher in the inspiration phase as compared to the expiration phase. It will be appreciated that the above-noted threshold of 400 Hz is not necessarily to be strictly applied as this value can be varied generally between 200 Hz and 900 Hz depending on the microphone acoustic characteristics, and specificities of the application. The BR of each breathing cycle was then calculated using equation (1).

$$BR = \sum_{400Hz}^{1000Hz} FFT(f) \Big/ \sum_{10Hz}^{400Hz} FFT(f) \qquad (1)$$

Using equation (1), the numerator represents the sum of FFT higher frequency magnitude bins which lie between 400 and 1000 Hz, and the denominator represents the sum of FFT lower frequency magnitude bins which lie between 10 and 400 Hz. Bins bellow 10 Hz were not included to avoid any DC contamination (referring to drift from a base line), and frequencies above 1000 Hz, can also, in some embodiments, be neglected since preliminary work (not shown) revealed insignificant spectral power at frequencies above 1000 Hz, in which case the computation may also be reduced. It will be appreciated, however, that higher frequencies above 1000 Hz may nonetheless be included depending on the calculation power of the instruments being used. To verify repeatability of the results, BR was calculated for 3 to 4 successive breaths in the included sequence and for a total of three sequences from different parts of the individual's sleep. A total of 100 breaths were collected from the 10 subjects. The mean number of breaths per subject was 10±0.

It will be appreciated by the person of ordinary skill in the art that other methods may be employed to achieve similar results. For example, while taking the ratios of sub-bands of an FFT spectrum to measure sub-band energy distributions provides a useful approach, other statistical methods and pattern recognition tools can be used to distinguish the relative distribution of sub-band ratios in FFT. Furthermore, FFT could also be replaced, in some embodiments, by implementing a series of digital filters that measure signal energy in the bands mentioned in this work, for example. Additionally, it will be appreciated that the entire digital processing stream, could, in some embodiments, be replaced by analogue signal processing techniques, such as by deploying a series of analog filters to achieve similar results.

Sleep Staging

Sleep stages were recorded during the course of the night using standard polysomnographic techniques that included electro-encephalography (EEG), electro-oculography and submental electro-myography (Rechtschaffen A and Kales A 1968 *A Manual of Standardized Terminology, Techniques and Scoring System for Sleep Stages of Human Subjects*. (Los Angeles: UCLA Brain Information Service/Brain Research Institute). The corresponding sleep stage for the selected breath samples was determined from the PSG recording (not shown).

Statistical Analysis

Data are expressed as mean±SD unless otherwise stated. A Wilcoxon Signed Ranks Test was performed using SPSS statistical package (SPSS, Chicago, Ill.). This test compares two related variables drawn from non-normally distributed populations. One-sample sing test was performed using Minitab 15 statistical package (Minitab Inc., State College, Pa.).

Comparison of Bands Ratio to Respiratory Inductance Plethysmography

Subjects

Healthy subjects at least 18 years of age were recruited with no history of respiratory or cardiopulmonary disease in addition to being free from prescribed medications. Data were collected from 15 subjects, 6 men and 9 women, healthy volunteers. Individuals used in the study were recruited by advertisement and were divided randomly intro 2 groups with 5 subjects in one group (test group) and 10 in the other (validation group). The data from the 5 subjects in the test group were used to examine acoustic characteristics of breathing phases, which were then incorporated into a method having an algorithm as described below. The resultant method was tested on the data of 10 subjects in the validation group to determine the validity of the method for determining the inspiration and expiration phases of an individual's breathing sounds.

Breath Sound Recording

Breath sounds in this particular example were recorded using a unidirectional, electret condenser microphone (Knowles Acoustics, Model MB6052USZ-2). The microphone's unidirectional pattern reduces the pickup of sounds from the sides and rear thereby improving isolation of the sound source. In this example, the microphone 12 was embedded in a respiratory mask 16, as shown in FIGS. 2*a* and 2*b*, that was modified by cutting away material so as to produce opening 14 such that only a structural frame remained to keep the microphone 12 in a fixed location relative the nostrils and the mouth of an individual 20 at a dimension "A" of approximately 3 cm in front of the individual's face as shown in FIG. 2a. The audio signal was digitized using an audio signal digitizing module and digitized sound data were transferred via transducing link 18 to a computer using a USB preamplifier and audio interface (M-Audio, Model Fast Track Pro USB) with a sampling rate of 22,050 Hz and resolution of 16 bits. Although various types of audio interfaces may be used, in the instant exemplary embodiment, an external audio interface was preferred over the other types of audio adapters, for example, built-in audio adapters due to the superior signal to noise (S/N) ratio of the external adaptor which was about 60 dB at 1 kHz. Sound recordings were then passed through a $4^{th}$ order band-stop digital filter with a centre frequency of about 60 Hz to suppress line interference.

Respiratory Inductance Plethysmography

Respiratory inductance plethysmography (RIP), (Respitrace Ambulatory Monitoring Inc., White Plains, N.Y., USA) was used to monitor respiratory pattern of individuals and the timing of the breathing phases. In contrast to other breathing monitoring apparatus such as pneumotacography, RIP has the advantage of being applied away from the face of an individual to allow capture of breathing phases. Briefly, RIP is a system comprising two flexible sinusoidal wires. Each wire is embedded in stretchy fabric band. One band 28 is placed around the chest of an individual and the other band 30 is placed around the abdomen of the individual as shown in FIG. 6a. The inductance of each band changes upon rib cage and abdomen displacements and generates a voltage signal proportional to its inductance. The signals from the RIP bands 28 and 30 were digitized at 150 Hz and stored in a computer memory as substantially describe above with reference to FIGS. 3 and 4. The electrical sum of the ribcage and abdominal signals is displayed on a readable medium, for example a computer screen or a physical plot, and provides the total thoracoabdominal displacement. The thoracoabdominal displacement recorded from the RIP system reflects changes of tidal volume during respiration.

In order to compare the inspiration and expiration phases of an individual's breathing to RIP, the microphone 12, as noted above, was coupled in this example to a modified mask 16 in front of the subject's face. Simultaneously, the RIP bands 28 and 30 were placed around the subject's chest and abdomen to measure thoracoabdominal motion as noted above. Recording were captured from both the microphone 12 and the RIP bands 28 and 30 simultaneously to assess the timing of breath sounds against the RIP waveform data.

Study Protocol

Individuals were studied in the supine position and were instructed to breathe normally. Microphone holding frame 16 was placed on individual's face. Each individual was asked to breath for two minutes at their regular breathing rate. In order to mimic all possible breathing conditions, the individuals were asked to breath through their nose only for half of the experiment time, and through their nose while mouth was slightly open in the other half. Incomplete breaths at the beginning and end of recording were discarded and all the breaths in between were included in the analysis.

Analysis of Breath Acoustics

In a first stage, spectral variables of breath sounds that characterize the inspiratory and expiratory phase components of a respiratory cycle were determined. The data of five subjects, 3 females and 2 males was chosen randomly from total 15 subjects and used to study the frequency characteristics of the acoustic signals of different respiratory phases. Inspiratory and expiratory segments of breath sounds were determined and extracted from the acoustic data by comparing it to the inspiratory (rising edge) and expiratory (falling edge) of the RIP trace as shown in FIG. 6b. A 25-second long recording of breath sounds and simultaneous summed thoracoabdominal RIP signals from a representative subject is shown, for example, in FIG. 6b. Dashed vertical lines are shown to separate inspiration and expiration phases of the second cycle at 32.

The first 10 complete breaths of each subject were analyzed, which yielded a total of 50 inspirations and 50 expirations acoustic data sets from the 5 subjects. Subsequently, the frequency spectrum of each phase was calculated separately using Welch's method (i.e. the average of a 2048-point Fast Fourier Transform (FFT) of sliding hamming windows with 50% overlap). FFT arrays were normalized in amplitude in order to compare the relative changes in power spectrum among resultant spectral arrays.

Using variables derived from frequency spectra of the 5 test individual's noted above, the inspiratory and expiratory phases of the breathing cycle were determined for the remaining 10 individuals in order to test the validity of the method. Furthermore, the method was tested for the ability to determine breathing phases from acoustic data independently from other inputs. The data analysis was performed with Matlab R2007b software package (Mathworks, Natick, Mass.).

Results

The characteristics of the individuals in this study are shown in Table 1. A total of 100 breaths were sampled from 10 patients with a mean number of 10 breaths per subject. Seventy percent of the breaths analyzed were from non-rapid-eye movement sleep (NREM), and 18% from rapid eye movement sleep (REM), and 12% while patients were awake according to the polysomnographic criteria.

TABLE 1

Characteristics of subjects.

| Subject | Age (years) | Sex | Body Mass Index |
|---------|-------------|-----|-----------------|
| Subject 1 | 51 | F | 39.1 |
| Subject 2 | 43 | M | 25.6 |
| Subject 3 | 49 | M | 23.7 |
| Subject 4 | 27 | M | 36.8 |
| Subject 5 | 64 | M | 26.3 |
| Subject 6 | 60 | M | 33.0 |
| Subject 7 | 68 | F | 28.5 |
| Subject 8 | 31 | M | 30.3 |
| Subject 9 | 48 | F | 31.6 |
| Subject 10 | 56 | M | 26.7 |

The bands ratio (BR) value was calculated for the inspiration phase bands ratio (BRi) 24, the expiration phase bands ratio (BRe) 26, and the interbreath pause bands ratio (BRp) 22 using equation 1. Inspiration and expiration showed consistent patterns of their frequency spectra as depicted in FIG. 7a for a given breathing cycle.

As shown in a representative example in FIG. 7b, there was a sharp narrow band of harmonics usually below 200 Hz for inspiration. The spectrum exhibited a valley between 200 Hz and 400 Hz and a peak again after 400 Hz as shown in FIG. 7b. Another variation of the inspiratory spectrum was the same initial narrow band followed by a relatively smooth spectrum without the 400 Hz drop (not shown). The expiratory spectrum, as shown in a representative example in FIG. 7c, on the other hand, formed a wider band that spanned frequencies up to 500 Hz and whose power dropped off rapidly above this frequency. The inspiratory spectrum (FIG. 7b) showed a peak close to the line frequency. The spectrum of the interbreath pause (not shown) was inconsistent and showed random variations without any consistent pattern. To rule out the effect of line frequency on inspiration bands ratio (BRi), a Wilcoxon signed rank test was used to test the relation between BRi and bands ratio interbreath pause (BRp). The test was significant (p<0.001), thus it was determined that BRi is different from BRp and that line interference does not significantly contribute to the frequency spectrum of inspiration.

The relationship between BRi and BRe was examined using the Wilcoxon Signed Ranks Test. The test showed that a BRi is not equal to BRe (P<0.001) with 95% of breaths having BRi greater than BRe. Since minute differences between BRi and BRe might be attributed to randomness, two thresholds of 50% and 100% difference between BRi and BRe were tested. The ratio BRi/BRe was calculated for each breath. By taking the ratio, BRi and BRe may be treated as dependant pairs. These ratios were then tested for being greater than 1.5 (50% difference) and greater than 2 (100% difference). The one-sample sign test showed that BRi/BRe is greater than 1.5 (p<0.001) and greater than 2 (p<0.001). In order to account for potential differences between subjects in the analysis, the mean BRi/BRe was calculated for each individual subject as displayed in Table 2. The one-sample sign test of the median was significant for mean BRi/BRe greater than 1.5 (p=0.001) and significant for mean BRi/BRe greater than 2 (p=0.001). Breaths that were drawn when subjects were polysomnographically awake did not differ significantly in terms of BRi/BRe from the rest of breaths (p=0.958) and, therefore, were included in the aforementioned analysis.

TABLE 2

Mean BRi/BRe for the subjects.

| Subject | Mean BRi/BRe (value ± SD) |
| --- | --- |
| Subject 1 | 1.66 ± 0.60 |
| Subject 2 | 2.30 ± 1.33 |
| Subject 3 | 2.43 ± 0.71 |
| Subject 4 | 3.17 ± 1.17 |
| Subject 5 | 2.67 ± 1.60 |
| Subject 6 | 3.86 ± 2.65 |
| Subject 7 | 23.01 ± 9.65 |
| Subject 8 | 14.99 ± 8.86 |
| Subject 9 | 15.66 ± 9.42 |
| Subject 10 | 11.56 ± 2.60 |

The sensitivity of this method was tested for each of the two cut-offs. Out of 100 breath samples, 90 had BRi 50% greater than BRe, and 72 had BRi 100% greater than BRe thereby giving an overall sensitivity of 90% and 72% respectively.

A total of 346 breaths met the inclusion criteria. The average number of breaths per individual was 23.0±7.79. Only the first 10 complete breaths were used to study the spectral frequency characteristics from the 5 individuals in the test group. From the validation group 218 breaths (i.e. 436 phases) were included in the analysis with an average of 21.8±8.2 breaths per subject.

Analysis of Breath Sounds

Figure 8A:
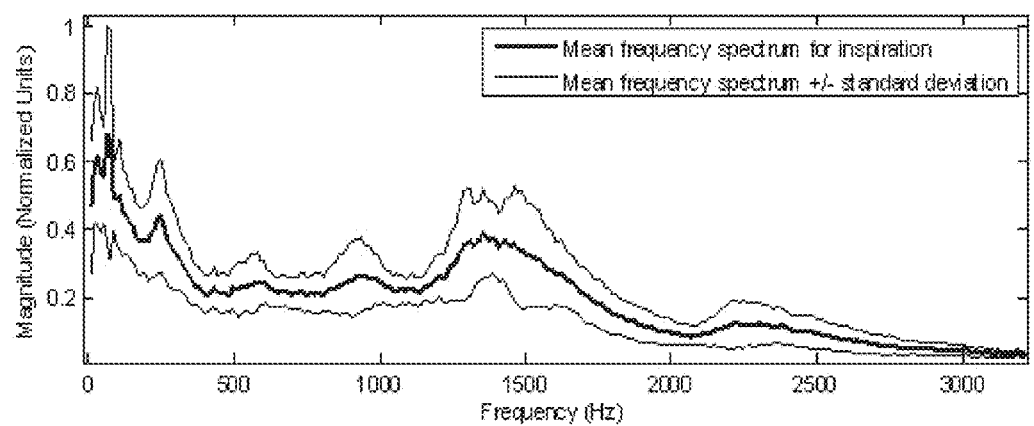
FIG. 8a is a representative plot of the average frequency magnitude spectrum and standard deviations of breathing sounds for inspiration in an individual.
Figure 8B:
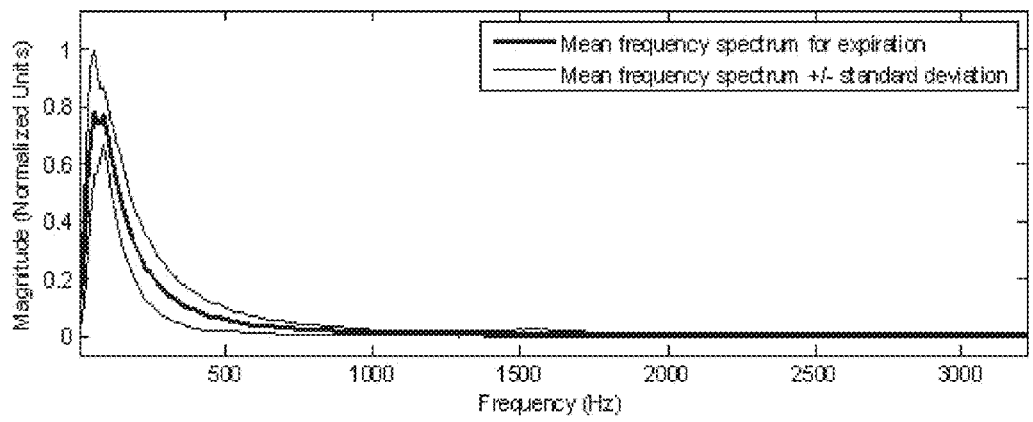
FIG. 8b is a representative plot of the average frequency magnitude spectrum and standard deviations of breathing sounds for expiration in an individual.

Data obtained from the test group of 5 individuals yielded 100 arrays of FFT magnitude bins normalized in amplitude with one half being from inspiratory acoustic inputs or phases and the other half from expiratory acoustic inputs or phases. The average spectrum of all normalized arrays belonging to the inspiration and expiration phases with the corresponding standard deviation are shown in FIGS. 8a and 8b respectively. FIGS. 8a and 8b demonstrate that the frequency spectra of the 2 phases have different energy distributions. The mean inspiratory spectrum, shown in FIG. 8a peaked between 30 Hz and 270 Hz. The spectrum exhibited flatness between 300 Hz and 1100 Hz before the next major peak with a center frequency of 1400 Hz. The expiratory spectrum, on the other hand, peaked between 30 to 180 Hz as shown in FIG. 8b. Its power dropped off exponentially until 500 Hz after which it flattened at low power.

The signal power above 500 Hz was consistently higher in inspiration than expiration. Since the ratio of frequency magnitudes between 500 to 2500 Hz, the higher frequency magnitude bins, to frequency magnitude between 0 to 500 Hz, the lower frequency magnitude bins, is higher during the inspiration phase than during the expiration phase for each breathing cycle, frequency ratio can be used to differentiate the two phases of the breathing cycle. This ratio is presented in equation (2) as the frequency bands ratio (BR).

$$BR = \sum_{500Hz}^{2500Hz} FFT(f) \Big/ \sum_{0Hz}^{500Hz} FFT(f) \quad (2)$$

The numerator of equation (2) represents the sum of FFT higher magnitude bins between 500 to 2500 Hz, and the denominator represents the sum of FFT lower magnitude bins below 500 Hz. BR was calculated for each of the six curves shown in FIGS. 8a and 8b which include the curve of the mean and the positive and negative standards deviation for both inspiration and expiration. These results are presented in Table 3:

TABLE 3

BR calculated for inspiration and expiration spectra.

| Inspiration | BR | Expiration | BR |
| --- | --- | --- | --- |
| Mean inspiration spectrum | 2.27 | Mean expiration spectrum | 0.15 |
| Mean inspiration spectrum + Std | 2.34 | Mean expiration spectrum + Std | 0.21 |
| Mean inspiration spectrum − Std | 2.14 | Mean expiration spectrum − Std | 0.02 |

The numbers in Table 3 represent the BR which is a ratio calculated from various curves.

Table 3 shows that the mean BR for inspiration (BRi) is 15.1 times higher than mean BR for expiration (BRe). BRi is higher than that for BRe. For example, by comparing the two extremes, 'BR for mean inspiration−Std', and 'BR for mean expiration+Std', as noted in Table 3 and shown in FIGS. 8a and 8b, BRi may be 10.2 time greater than that for BRe. However, other predetermined multipliers may be acceptable for determining the inspiration and expiration phases of breathing. For example, the multiplier maybe from about 1 to about to about 20. Therefore, the frequency-based variable BR may be used to distinguish the various phases of a given breathing cycle.

Figure 9:
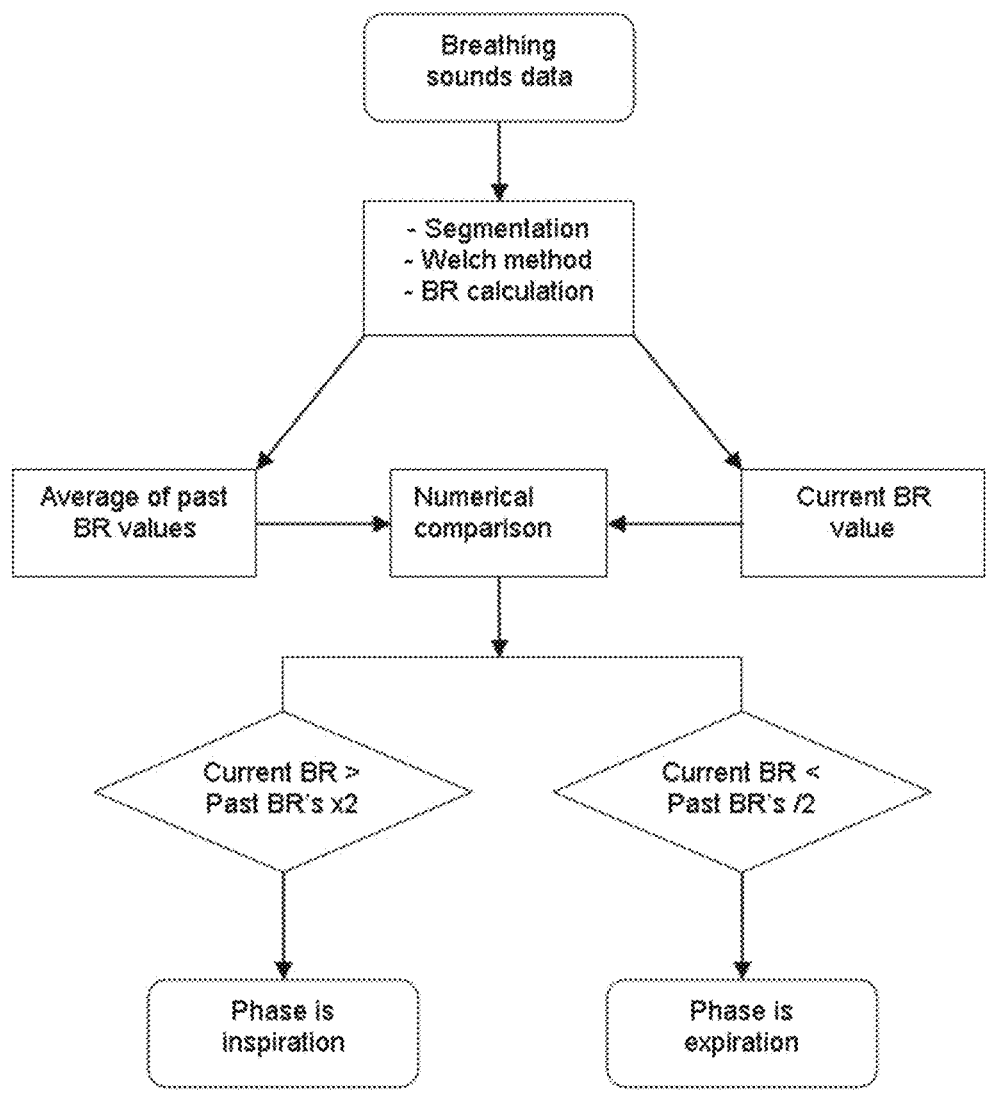
FIG. 9 is a flow diagram of the method for monitoring, identifying and determining the breathing phases from breathing sound data.
Figure 10A:
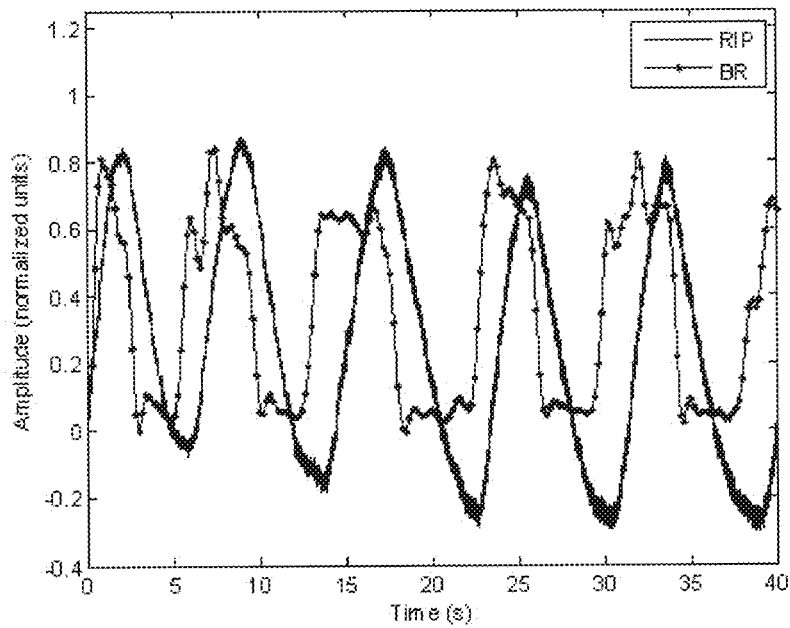
FIG. 10a is representative amplitude versus time plot of breathing sound data and simultaneous RIP data.
Figure 10B:
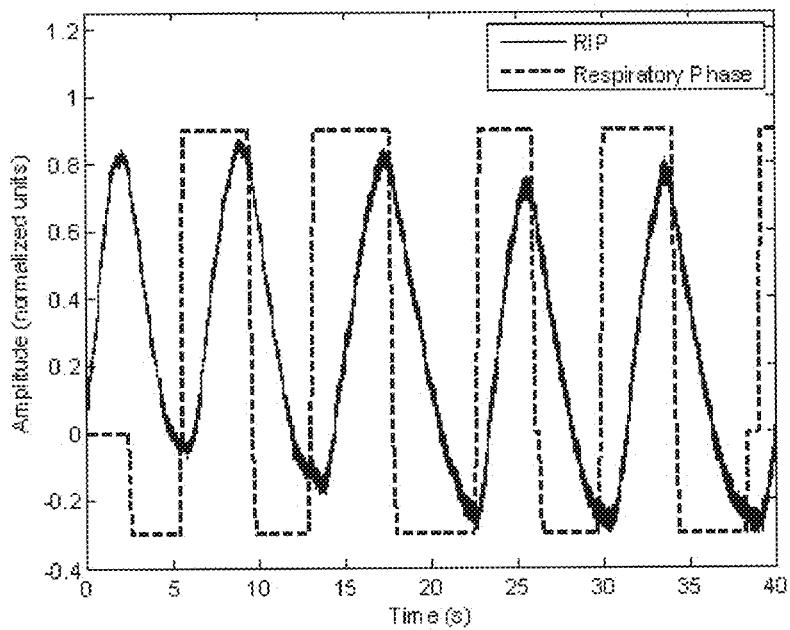
FIG. 10b is a comparative plot of the RIP data of FIG. 10a and the breathing phases found using the method of FIG. 9 for monitoring, identifying and determining breathing phases wherein the positive values of the dashed line represent inspiration and the negative values of the dashed line represent expiration.

In order to validate the results of the procedure as found using the test group, the BR parameters as determined above were utilized to track the breathing phases in the individuals in the validation group. A method that depends on past readings of acoustic data was developed to predict the current phase. A flow diagram of this method is shown schematically in FIG. 9. For example, a benefit of using past values rather than post-processed statistics is that the technique can be adopted for real-time implementation. According to this exemplary embodiment, the acoustic data stream is segmented into 200 ms segments. However, it may be desirable for the segments to be of a length greater than or less 200 ms. For example the segments may be from about 50 ms to about 1 second. Preferably, the segments are from about 100 ms to about 300 ms. Each segment is then treated as described above in relation to the test group. For example, Welch's method was applied to calculate frequency spectrum and it's BR, a first bands ratio (first BR). Subsequently the mean BR of the past 1.4 seconds (7 segments×200 ms) or the mean of all the past BR's, whichever is greater, was calculated. Each newly found BR, said first BR, was then compared with the past BR average or mean bands ratio. If the first BR is greater than the mean BR by at least a predetermined multiplier, then it is labeled as inspiration. The predetermined multiplier may be from about 1.1 to about 10. Preferably the multiplier is from about 1 to about 5. Most preferably, the multiplier is from about 1.5 to 2. For example, if the first BR is twice the past 1.4 seconds BR average (mean BR) then it is labeled as inspiration. Likewise, if the first BR is less than mean BR by at least a predetermined multiplier, then it is labeled as expiration. Therefore, for example, a segment is labeled as expiration if the corresponding BR is 2 times below the average of the past two segments. FIG. 10a shows an exemplary representative plot of an embodiment of all BR values calculated from the acoustic data with the corresponding RIP for comparison. Visual examination shows that there is a correlation between BR waveform and its RIP counterpart. Averaging of the BR's is performed in order to smooth out intra-phase oscillations in BR such as in the case of the BR curve at time 5-10 seconds seen in FIG. 10a The method was tested prospectively on the breathing acoustic data of 10 subjects in the validation group. The breathing phases found using the presently described method as applied to the data of FIG. 10a are shown in FIG. 10b. With reference to FIG. 10b, the dashed line represents the respiratory or breathing phases found utilizing the currently described method. Out of 436 breathing phases, 425 breathing phases were labeled correctly, 8 phases were partially detected, and 3 phases were labeled as being the opposite phases. Therefore, utilizing the method, about 97.4% of the breathing phases were detected correctly using acoustic data as compared with RIP trace.

With reference to FIG. 10b, the breathing cycles are shown as a processed wave amplitude versus time plot. The processed wave amplitude data are shown by the dashed line and indicate the respiration phase of an individual's breathing. In an exemplary embodiment, the processed wave amplitude versus time plot may be displayed on a display module such as that shown in FIG. 3 at 1.1. The processed wave amplitude versus time plot may also be, in some exemplary embodiments, provided to an operator by way of an information relay or relaying module in a printed form or other suitable form, for example audio cues, such that the breathing of an individual may be monitored in accordance with the method by an operator. In some exemplary embodiments, the information relay module may display or provide the processed data in terms or inspiration and/or expiration indicia.

The frequency spectrum of inspiration may be characterized by a narrow band below 200 Hz, a trough starting from about 400 Hz to about 600 Hz. In the exemplary embodiments noted herein, the trough begins at about 400 Hz in one, the first, embodiment (FIG. 7b) and at about 500 Hz in another, second, embodiment (FIG. 8a). A wider but shorter peak above may be seen at about 400 Hz to about 600 Hz. The peak is seen at about 400 Hz in the first embodiment (FIG. 7b) and at about 500 Hz in the second embodiment (FIG. 8a). In the embodiments noted herein, a smooth frequency distribution is noted after the decline of the initial narrow peak (FIGS. 7b and 8a). However, it maybe desirable in order embodiment to utilize various other frequencies and frequency ranges, for example by way of illustration and not limitation, greater than or less than about 400 Hz or 500 Hz.

Expiration, on the other hand, may be characterized by a wider peak with a relatively sharp increase from about 10 to 50 Hz and a smooth drop from about 50 to 400 Hz as seen in the first embodiment shown in FIG. 7c or in the second exemplary embodiment as shown in FIG. 8b, above about 500 Hz. There is a relatively sparse frequency content above about 400 Hz in the first exemplary embodiment of FIG. 7c and likewise in the exemplary second embodiment of FIG. 8b above about 500 Hz. A cut-off point of 400 Hz in the first exemplary embodiment and 500 Hz in the second exemplary embodiment was chosen to distinguish between inspiration and expiration phases based upon these observations. Although recordings of breathing sounds have frequency content up to 10 kHz, most of the power lies below 2 kHz, and therefore higher frequencies may not be required to be considered. Additionally, frequencies below 10 Hz may also be excluded in order to avoid the effect of baseline shift (DC component). Therefore, a considering the aforementioned factors a simple ratio between the sums of magnitudes of bins of higher frequency (above about 400 Hz in the first embodiment and above about 500 Hz in the second embodiment) to those of lower frequency (about 10 Hz to about 400 Hz in the first embodiment and about 0 Hz to about 500 Hz in the second embodiment) distinguished the inspiration phase from the expiration phase of breathing. However, as the preceding embodiments are for exemplary purposes only and should not be considered limiting, other frequency ranges may be utilized. Additionally, the method may be fine tuned and/or modified as desired according to the location and type of the microphone.

As shown by way of the exemplary embodiments disclosed herein expiration may have a lower BR value than inspiration. Therefore the ratio of BRi/BRe for each breathing cycle was calculated in order to determine the intra-breath relationship between BRi and BRe. BRi/BRe was surprisingly found to be significantly greater than one. In other words, for each individual breath BRi is significantly higher than BRe. Since this exemplary method employs relative changes in spectral characteristics, it is not believed to susceptible to variations in overall signal amplitude that result from inter-individual variations.

The sensitivity of the exemplary method in certain embodiments is about 90% and 72% for 1.5-fold and 2-fold difference between the two phases respectively. However, there may be a trade-off between sensitivity and robustness; choosing a higher frequency cut-off may make the method more specific and less susceptible to noise but sensitivity may decrease.

As disclosed herein, a method for monitoring breathing by examining BR variables of short segments of breathing acoustic data is provided. The data was divided into 200 ms segments with subsequent Welch's method applied on each segment. However, longer or shorter segments may be desirable in various applications. The method involves applying FFT's on each segment and averaging the resultant arrays. Averaging FFT results within the segment further provides a random-noise-cancelling effect. The method of utilizing BRi/BRe in order to determine the breathing phase sound data a showed correlation with thoracoabdominal movement as seen in FIGS. 10a and 10b. Therefore, the currently provided method may be useful for monitoring, identifying and determining the breathing cycle phases of an individual. The method may, for example, be utilized for monitoring, identifying and determining the breathing phase from a pre-recorded audio track, or the method may also be utilized, for example for real-time monitoring of breathing.

For example, in a real-time breathing monitoring situations, BR variables may be examined in sequence and each BR variable is compared with a predetermined number of preceding BR values or preceding BR values. The preceding BR variables may be subject to a moving averaging window with the length of a breathing phase, which is approximately, for example 1.4 seconds. However, a longer or shorter window may be utilized as required. Although in one exemplary embodiment, there is shown a 10-15 fold difference in the BR between the breathing phases, a lower threshold may be considered. For example, since the moving averaging window incorporates transitional BR points between the inspiration and expiration phases which dilute the BR average of a pure breathing phase a greater or less fold-difference than that noted herein in the exemplary embodiments may be observed. Accordingly, an empirical threshold of 2 was chosen for the testing and illustration purposes of an example of the present method. Utilizing the method as provided herein, about 97.4% of the breathing phases were classified correctly. It will be appreciated that while a moving averaging technique is proposed above, other techniques may be applied to distinguish BR variables that have higher values (inspiration) from those that have lower ones (expiration). Exemplary techniques may include, but are not limited to k-means clustering, fuzzy c-means, Otsu clustering, simple thresholds, etc.

The method and apparatus as defined herein may be useful for determining the breathing phases in sleeping individuals as well as being useful for determining the breathing phases of awake individuals. It provides a numerical method for distinguishing each phase by a comparison of segments of the frequency spectrum. The present exemplary method may, if desired, be used for both real-time and offline (recorded) applications. In both cases (online and offline) phase monitoring may be accomplished by tracking fluctuations of BR variables.

The present exemplary method may be applied to other applications which require close monitoring of respiration such as in intensive care medicine, anesthesia, patients with trauma or severe infection, and patients undergoing sedation for various medical procedures. The present exemplary method and apparatus provides the ability of integrating at least one transducer, such as a microphone, and a transducing link with a medical mask, for example as shown in FIGS. 2a and 2b, and 11 to 22, thereby eliminating the need to attach a standalone transducer on the patients' body to monitor respiration. The present exemplary method may also be used for accurate online breathing rate monitoring and for phase-oriented inhaled drug delivery, for classification of breathing phases during abnormal types of breathing such as snoring, obstructive sleep apnoea, and postapnoeic hyperventilation.

Thus, the present method may thus be useful to classify breathing phases using acoustic data gathered from in front of the mouth and nostrils distal to the air outlets of an individual. A numerical method for distinguishing each phase by simple comparison of the frequency spectrum is provided. Furthermore, a method which employs relative changes in spectral characteristics, and thus it is not susceptible to variations in overall signal amplitude that result from inter-individual variations is provided and may be applied in real-time and recorded applications and breathing phase analysis.

While the present disclosure describes various exemplary embodiments, the disclosure is not so limited. To the contrary, the disclosure is intended to cover various modifications and equivalent arrangements included within the spirit and scope of the appended claims. The scope of the following claims is to be accorded the broadest interpretation so as to encompass all such modifications and equivalent structures and functions.

The invention claimed is:

1. A mask to be worn on a subject's face for use in respiratory monitoring, the mask comprising:
    an airflow transducer responsive to airflow pressure variations for generating a signal representative of an airflow amplitude; and
    a support structure shaped and configured to rest on, the subject's face, and comprising two or more outwardly projecting air guiding or redirecting limbs that, upon positioning the mask, converge into a transducer supporting portion supporting said airflow transducer at a distance from a nose and mouth area of the subject's face, said two or more outwardly projecting air guiding or redirecting limbs shaped to guide or redirect airflow produced by the subject while breathing toward said air low transducer when said support structure rests on the subject's face, thereby improving responsiveness of said airflow transducer to airflow produced by the subject while breathing;
    wherein the mask is an open mask having openings defined between said two or more limbs to allow air to exit through said openings.

2. The mask of claim 1, said airflow transducer comprising one or more transducers responsive to sound and airflow, the mask thereby allowing for monitoring via said one or more transducers of both sound and airflow produced by the subject while breathing.

3. The mask of claim 2, said one or more transducers comprising a first transducer predominantly responsive to airflow and a second transducer predominantly responsive to sound.

4. The mask of claim 1, each of said two or more outwardly projecting limbs having, along at least a portion thereof, an inward-facing channel defined therein for channeling at least a portion of said airflow toward said airflow transducer.

5. The mask of claim 4, said transducer supporting portion having a funneling shape fluidly extending from each said inward-facing channel to further funnel channeled air how toward said airflow transducer.

6. The mask of claim 1, wherein said two or more outwardly projecting limbs comprise two opposed side limbs and a central limb converging into said transducer supporting portion to form a tripod-like structure extending from said area when the mask is in position.

7. The mask of claim 1, said transducer supporting portion having a funneling shape oriented so as to funnel at least a portion of said airflow toward said airflow transducer.

8. The mask of claim 7, wherein said funneling shape is defined by a substantially concave structure sized and oriented so as to enhance capture of both oral and nasal airflow.

9. The mask of claim 1, said transducer supporting portion having a funneling shape oriented so as to funnel at least a portion of said airflow toward said airflow transducer, wherein said funneling shape fluidly extends into an inward-facing channel defined along at least a portion of each of said two or more outwardly projecting limbs, whereby said at least portion of said airflow is channeled thereby toward said airflow transducer.

10. The mask of claim 1, consisting of a self-contained mask, further comprising a recording device mounted to said support structure and operatively coupled to said airflow transducer for recording said airflow in operation, wherein said recording device is further configured for transferring said recording for processing by a remote respiratory disorder diagnostic system.

11. The mask of claim 10, wherein said recording device comprises one or more of a removable data storage medium, a wireless communication device and a wired communication port for digitally transferring said recording.

12. The mask of claim 1, said support structure delineating said area.

13. The mask of claim 1, further comprising a face-framing portion from which said two or more limbs extend, said face-framing portion delineating an area by at least partially circumscribing said subject's face, wherein said face-framing portion is shaped to contour the subject's face when in position thereby facilitating proper positioning of the mask.

14. The mask of claim 1, wherein said two or more limbs define said openings.

15. The mask of claim 1, wherein said airflow transducer is selected from the group consisting of a microphone, a pressure sensor and an airflow sensor.

16. The mask of claim 1, wherein said transducer supporting portion comprises one or more support limbs supporting said transducer across an aperture defined within said support structure thereby allowing evacuation of airflow directed toward said airflow transducer by said air guiding or redirecting limbs, thus reducing airflow resistance.

17. The mask of claim 16, said one or more support limbs comprising two or more bridging limbs extending outwardly from said support structure to support said airflow transducer across said aperture.

18. The mask of claim 1, wherein said support structure is shaped and configured such that said outwardly projecting air guiding and redirecting limbs guide and redirect said airflow unobstructed to said transducer.

19. The mask of claim 1, wherein said airflow transducer is a microphone.

20. A mask to be worn on a subject's face for use in respiratory monitoring, comprising:
- an airflow transducer to measure airflow pressure variations, the airflow transducer generating a signal representative of an airflow amplitude;
- a support structure having two or more outwardly projecting air guiding limbs that converge into a transducer supporting portion supporting the airflow transducer at a predefined distance from a nose and mouth area of the subject's face;
- the two or more outwardly projecting air guiding limbs shaped redirecting airflow toward the airflow transducer thereby improving responsiveness of the airflow transducer to airflow;
- wherein the mask is an open structured mask having openings defined between said two or more limbs to allow air to exit through said openings, and is not a closed mask which captures and contains the subjects breath;
- the two or more outwardly projecting air guiding limbs shaped to guide airflow produced by the subject while breathing, toward the airflow transducer when the support structure rests on the subject's face thereby improving responsiveness of the airflow transducer to airflow produced by the subject while breathing.

* * * * *